US006559295B1

(12) United States Patent
Barrow et al.

(10) Patent No.: US 6,559,295 B1
(45) Date of Patent: May 6, 2003

(54) MYCOBACTERIUM FOL A GENE THAT ENCODES FOR THE ENZYME DIHYDROFOLATE REDUCTASE

(75) Inventors: William W. Barrow, Hoover, AL (US); Sabrina Z. Van Ginkel, Homewood, AL (US); Thomas P. Dooley, Vestavia Hills, AL (US); William J. Suling, Pehlam, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 09/372,591

(22) Filed: Aug. 12, 1999

Related U.S. Application Data

(62) Division of application No. 08/990,791, filed on Dec. 15, 1997, now Pat. No. 6,229,001.
(60) Provisional application No. 60/034,725, filed on Jan. 3, 1997, and provisional application No. 60/039,737, filed on Feb. 14, 1997.

(51) Int. Cl.[7] ........................ C07H 21/02; A61K 39/40; A61K 39/12; A61K 39/02; A61K 39/04

(52) U.S. Cl. ................ 536/23.1; 424/168.1; 424/199.1; 424/200.1; 424/248.1; 435/6; 435/7.6; 435/69.1; 435/91.1; 435/863; 435/864; 536/22.1; 536/23.2; 536/23.6

(58) Field of Search ........................... 424/168.1, 199.1, 424/200.1, 248.1; 435/6, 7.6, 69.1, 91.1, 91.4, 252.3, 253.1, 419, 863, 864, 865, 866; 536/22.1, 23.1, 23.2, 23.6; 935/22, 23

(56) References Cited

U.S. PATENT DOCUMENTS

| | | | | |
|---|---|---|---|---|
| 4,512,992 A | 4/1985 | Duch et al. | ................. | 514/258 |
| 4,956,284 A | 9/1990 | Phillips et al. | .............. | 435/123 |
| 4,962,111 A | 10/1990 | Welch et al. | ............... | 514/255 |
| 4,997,835 A | 3/1991 | Schaper et al. | ............. | 514/248 |
| 5,084,458 A | 1/1992 | Schaper et al. | ............. | 514/259 |
| 5,527,770 A | 6/1996 | Platt | .............................. | 514/2 |

FOREIGN PATENT DOCUMENTS

| | | | |
|---|---|---|---|
| DE | 4027588 | 8/1990 | ......... C07D/239/48 |
| EP | 0542497 | 11/1992 | ......... C07D/487/04 |
| WO | WO8503639 | 8/1985 | .......... A61K/39/04 |
| WO | WO8802027 | 3/1988 | ........... C12N/15/00 |

OTHER PUBLICATIONS

Locher H.H., et al. Antibacterial activities of epiroprim, a new dihydrofolate reductase inhibitor, alone and in combination with dapsone. Antimicrobial Agents and Chemotherapy. vol. 40, No. 6, pp. 1376–1381, Jun. 1, 1996.*

Kansy, M., et al. Synthesis of new 2,4–diamino–5–benzylpyrimidies active against various bacterial species. European Journal of Medicinal Chemistry, vol. 27, No. 3, pp. 237–244, Jun./1996.*

Czaplinski, K–H, et al.: "New benzylpyrimidines: inhibition of DHFR from various species. QSAR,CoMFA and PC analysis," European Journal of Medicinal Chemistry, vol. 30, No. 10, 1995, pp. 779–787.

Hartman, P.G.: "Molecular aspects and mechanisms of action of dihydrofolate reductase inhibitors," Journal of Chemotherapy, vol. 5, No. 6, 1993, pp. 369–376.

Kansy, M. et al.: "Synthesis of new 2,4–diamino–5–benzylpyrimidines active against various bacterial species," European Journal of Medicinal Chemistry, vol. 27, No. 3, 1992, pp. 237–244.

Reddy, L.V. et al.: "Detection of Pneumocystis carinii in a rat model of infection by polymerase chain reaction," Molecular and Cellular Probes, vol. 6, No. 2, Apr. 1992, pp. 137–143.

Scuderi,J.D.: "Molecular genetic and biochemical analysis of thymidylate synthase and dihydrofolate reductase from mycobacteria," 1996, Ph.D. Thesis, Yeshiva Univ., New York, NY, pp. 130–137; 144–145; 111–154; 1–27; I–V.

Seydel, J.K.: "In vitro and in vivo results of brodimoprim and analogue alone and in combination against E. coli and mycobacteria," Journal of Chemotherapy, vol. 5, No. 6, 1993, pp. 422–429.

Shah, L.M., et al.: "Enhanced in vitro activity of WR99210 in combination with dapsone against Mycobacterium avium complex," Antimicrobial Agents and Chemotherapy, vol. 40, No. 11, 1996, pp. 2644–2645.

Sirawaraporn, W.: "Purification and characterization of dihydrofolate reductase from wild–type and trimethoprim-resistant Mycobacterium smegmatis," Experimental Parasitology, vol. 72, No. 2, 1991, pp. 184–190.

Then, R.L.: "History and future of antimicrobial diaminopyrimidines," Journal of Chemotherapy, vol. 5, No. 6, 1993, pp. 361–368.

(List continued on next page.)

*Primary Examiner*—Rodney P Swartz
(74) *Attorney, Agent, or Firm*—Heller Ehrman White & McAuliffe, LLP

(57) ABSTRACT

The invention relates to the nucleic acid sequence and amino acid sequence of dihydrofolate reductase (DHFR) from mycobacteria and to expression of recombinant DHFR protein. Utilizing the recombinant protein, novel therapies and diagnostic strategies can be developed and selective antimycobacterial compositions can be designed and utilized to treat mycobacterial infections in patients. This invention includes all or portions of novel recombinant nucleic acids encoding DHFR for mycobacteria such as *M. avium*, to novel recombinant DHFR peptides produced by such sequences, and to vaccines, diagnostic kits, cells and therapies utilizing these peptides and nucleic acid sequences. The present invention relates to methods for using the sequences of the present invention to develop drugs specific to *M. avium* and other mycobacteria, to identify and sequence corresponding sequences in species other than *M. avium*, as well as diagnostic and treatment methods incorporating the disclosed sequences and peptides.

23 Claims, 9 Drawing Sheets

OTHER PUBLICATIONS

Zywno–Van Ginkel, et al.: "Mycobacterium avium dihydrofolate reductase (folA) gene, complete cds".

Zywno–Van Ginkel, et al.: "Identification and cloning of the Mycobacterium avium folA gene required for dihydrofolate reductase," FEMS Microbiology Letters, vol. 156, No. 1, Nov. 1, 1997, pp. 69–78.

W. Sirawaraporn et al., "Purification and Characterization of Dihydrofolate Reductase from Wild–Type and Trimethoprim–Resistant *Mycobacterium smegmatis", Experimental Parasitology* 72:184–190 (1991).

GenBank Database Accession No. X59271, "Mycobacterium tuberculosis folA gene (putative) for dihydrofolate reductase", Jun. 9, 1991.

GenBank Database Accession No. AL008967, Mycobacterium tuberculosis sequence v002, Nov. 18, 1997.

Czaplinski, K–H. et al., "New benzylpyrimidines: Inhibition of DHFR from various species. QSAR, CoMFA and PC analysis", Eur.J.Med.Chem. 1995, vol. 30, pp. 779–787.

Kansy, M. et al., "Synthesis of new 2,4–diamino–5–benzylpyrimidines active against various bacterial species", Eur.J.Med.Chem. 1992, vol. 27, pp. 237–244.

Philipp, W.J., "An integrated map of the genome of the tubercle bacillus, Mycobacterium tuberculosis H37Rv, and comparison with Mycobactrium leprae", Proc. Nat'l. Acad. Sci., Apr. 1996, vol. 93, No. 7, pp. 3132–3137.

Scuderi, J.D., "Molecular genetic and biochemical analysis of thymidylate synthase and dihydrofolate reductase from mycobacteria," Dissertation Abstracts International, 1996, vol. 57, No. 8B, pp. 4874B–4875B.

International Search Report for International Application No. PCT/US97/23557 dated Jun. 15, 1998.

Scuderi, Jospeh D., Dissertation entitled "Molecular Genetic and Biochemical Analysis of Thymidylate Synthase and Dihydrofolate Reductase from Mycobacteria", 1996.

* cited by examiner

```
  1 GACGTCGTGGTGCACAACTACGATCCGCACCCGGCCATCAAGGCCCCCGTCGCGGTATGA  60
                                                           M  T
 61 CCCGTGCCGAGGTGGGCCTGGTGTGGGCCCAGTCGACGTCTGGCGTCATCGGCCGCGGCG 120
      R  A  E  V  G  L  V  W  A  Q  S  T  S  G  V  I  G  R  G  G
121 GTGACATCCCGTGGAGCGTGCCCGAGGACCTCACCCGGTTCAAAGAGGTGACCATGGGGC 180
      D  I  P  W  S  V  P  E  D  L  T  R  F  K  E  V  T  M  G  H
181 ACACCGTGATCATGGGCCGGCGGACCTGGGAGTCGTTGCCGGCCAAGGTGCGGCCGCTGC 240
      T  V  I  M  G  R  R  T  W  E  S  L  P  A  K  V  R  P  L  P
241 CCGGCCGGCGCAACGTGGTGGTGTCCCGCCGGCCCGACTTCGTCGCCGAGGGGGCGCGGG 300
      G  R  R  N  V  V  V  S  R  R  P  D  F  V  A  E  G  A  R  V
301 TGGCCGGGTCGCTGGAGGCGGCCCTCGCGTACGCCGGGAGCGACCCGGCGCCGTGGGTGA 360
      A  G  S  L  E  A  A  L  A  Y  A  G  S  D  P  A  P  W  V  I
361 TCGGCGGCGCGCAGATCTATCTGCTGGCGCTGCCCCATGCCACCCGCTGCGAGGTCACCG 420
      G  G  A  Q  I  Y  L  L  A  L  P  H  A  T  R  C  E  V  T  E
421 AAATCGAGATCGACCTGCGCCGCGACGACGACGACGCGCTGGCGCCGGCGCTGGACGACA 480
      I  E  I  D  L  R  R  D  D  D  D  A  L  A  P  A  L  D  D  S
481 GCTGGGTAGGCGAGACGGGCGAGTGGCTGGCCAGCCGCTCCGGGCTGCGGTACCGGTTCC 540
      W  V  G  E  T  G  E  W  L  A  S  R  S  G  L  R  Y  R  F  H
541 ACAGCTACCGTCGGGACCCGCGCTCTTCCGTTCGCGGCTGTTCGCCCTCACGCCCGAGCT 600
      S  Y  R  R  D  P  R  S  S  V  R  G  C  S  P  S  R  P  S  *
601 GACATACTCGGACGCGGGGGTCGGTCACACACCGTCTACCAGCCGCTGTTCGGGAAAAGG 660
```

FIG. 7

```
M. avium       M T R A E V G L V W A Q S T S G V I G
                         •   | •   | |   |   | • |
M. smegmatis           S M S L I ? A Q ? T G G I I S
```

FIG. 9

MYCOBACTERIUM FOL A GENE THAT ENCODES FOR THE ENZYME DIHYDROFOLATE REDUCTASE

This application is a divisional of application Ser. No. 08/990,791, filed Dec. 15, 1997 now U.S. Pat. No. 6,229, 001, entitled Mycobacterium FOL A Gene That Encodes For The Enzyme Dihydrofolate Reductase; and claims the benefit of provisional applications No. 60/034,725, filed Jan. 3, 1997 and Serial No. 60/039,737, filed Feb. 14, 1997.

BACKGROUND OF THE INVENTION

1. Field of the Invention

This invention relates to novel recombinant nucleic acids encoding the enzyme dihydrofolate reductase (DHFR) from mycobacteria, to novel recombinant DHFR peptides produced by such sequences, and to vaccines, diagnostic kits, cells and therapies utilizing these peptides and nucleic acid sequences. The invention is also directed to methods for using the sequences and peptides to develop drugs specific to *M. avium* and other species of mycobacteria, to identifying other DHFR sequences and peptides, as well as diagnostic and treatment methods incorporating the disclosed sequences and peptides.

2. Description of Background

The *Mycobacterium avium* complex represents one of the most serious opportunistic infections and is often associated with advanced stages of autoimmune deficiency syndrome or AIDS (J. J. Ellner et al., J. Infect. Dis. 163:1326–35, 1991; J. A. Havlok, Jr. et al., J. Infec. Dis. 165:577–80, 1992; C. C. Hawkins et al., Ann. Intern. Med. 105:184–88, 1986; D. S. O'Brien et al., Am. Rev. Respir. Dis. 135:1007–14, 1989; N. Rastogi et al., Res. Microbiol. 145:167–261, 1994). Unlike *Mycobacterium tuberculosis*, which can be successfully treated with two or three drug combinations (except for multidrug resistant *M. tuberculosis*; MDR-TB), the *M. avium* complex is resistant to many antimycobacterial agents (B. D. Agins et al., J. Infect. Dis. 159:784–87, 1989; C. Benson et al., Sixth International Conference on AIDS, San Francisco, 1990; J. Chiu et al., Ann. Intern. Med. 113:358–61, 1990; F. De Lalla et al., Antimicrob. Agents Chemother. 36:1567–69, 1992; L. Heifets et al., Antimicrob. Agents Chemother. 37:2364–70, 1993; D. Y. Rosenzweig, Amer. Rev. Resp. Dis. 113(Suppl.):55, 1976). Drug resistance in *M. avium* is still considered an inherent property of the wild type organism (S. L. Morris et al., Complex. Res. Microbiol. 147:68–73, 1996), resulting in large part from the refractory nature of the organism's cell envelope (H. L. David, Rev. Infect. Dis. 3:878–84, 1981; N. Rastogi et al., Res. Microbiol. 145:243–52, 1994; N. Rastogi et al., Antimicrob. Agents Chemother. 20:666–77, 1981). Although *M. avium*infections in AIDS patients are treated with 3–6 different drugs, the long term prognosis is still poor (B. D. Agins et al., J. Infect. Dis. 159:784–87, 1989; C. Benson et al., Sixth International Conference on AIDS, San Francisco, 1990; J. Chiu et al., Ann. Intem. Med. 113:358–61, 1990; F. De Lalla et al., Antimicrob. Agents Chemother. 36:1567–69, 1992; J. J. Ellner et al., J. Infect. Dis. 163:1326–35, 1991).

Tuberculosis is a disease of worldwide significance and notoriety. At any one time, about one-third of the world is infected with *M. tuberculosis* resulting in eight million new cases of tuberculosis and 2.9 million deaths annually (A. Arachi, Tubercle. 72:1–6, 1991). It is estimated that about 0.3% of U.S. residents are infected and at risk to develop active disease (CDC 1996, CDC Revises HIV Infection Estimates. HIV/AIDS Prevention. August:2). This risk becomes even greater if the person is co-infected with the human immunodeficiency virus (HIV). If so, estimates indicate that progression to tuberculosis will occur in about 30% of those cases and the risk for developing tuberculosis becomes 113 times greater (tuberculosis., N.a.p.t.c.m.-r., MMWR. 41 RR-11:1–71, 1992).

As the projected figure for HIV infections is more than 20 million by the year 2000, it is probable that the number of tuberculosis cases worldwide will also increase. Even in 1991, the figure for people co-infected with HIV and *M. tuberculosis* was estimated to be 3.1 million (J. F. Murray, Bull. Int. Union Tuberc. Lung Dis. 66:21–15, 1991). In addition, life-threatening strains of MDR-TB are appearing. Some of these strains can result in a high mortality rate (e.g. 72–89%), with death occurring in a short period (e.g. 4–16 weeks) (CDC, Mortal. Morbid. Weekly Rep. 39:718–22, 1990; CDC, Mortal. Morbid. Weekly Rep. 40:649–652, 1991; B. R. Edlin et al., New Engl. J. Med. 326:1514–21, 1992). In summary, the impact of tuberculosis on the world today can best be appreciated by the fact that the World Health Organization declared tuberculosis a global public health emergency, a distinction never before given to any other disease (WHO., Soz Praventivmed. 38:251–52, 1993). Consequently, the development of new antimycobacterial drugs is an important research endeavor.

The dihydrofolate reductase (DHFR) enzyme is an important target for medicinal chemistry (K. Bowden et al., J. Chemother. 5:377–88, 1993) and DHFR inhibitors have been used in anticancer therapy (e.g. methotrexate (W. A. Bleyer, Cancer Treat. Rev. 41:36–51, 1978)), antibacterial therapy (e.g. trimethoprim (M. Finland et al., J. Infect. Dis. 128:S425–816, 1973)), and antimalarial therapy (e.g. pyrimethamine (A. K. Saxena, Prog. Drug Res. 30:221–80, 1986)). Dihydrofolate reductase is present in all cells and is necessary for the maintenance of intracellular folate pools in a biochemically active reduced state (M. McCourt et al., J. Am. Chem. Soc. 113:6634–39, 1991). Inhibition of the enzyme is effective because binding affinities for substrate analogs are so great that such analogs are not readily displaced by the natural substrates. Enzyme inhibition results in the depletion of intracellular reduced folates that are required for one carbon transfer reactions, which in turn are important for the biosynthesis of thymidylate, purine nucleotides, methionine, serine, glycine and many other compounds needed for RNA, DNA, and protein synthesis. FIG. 1 depicts DHFR's role in the biosynthesis of tetrahydrofolate and cell metabolism. (P. G. Hartman, J. Chemother. 5:369–76, 1993). Some bacteria have an uptake system for folates, but most have to synthesize folates de novo by reduction of dihydrofolate to tetrahydrofolates.

Although DHFR is not a new drug target, enthusiasm in the development of improved derivatives to inhibit DHFR is very intense, (D. P. Baccanari et al., J. Chemother. 5:393–99, 1993; K. Bowden et al., J. Chemother. 5:377–88, 1993; M. McCourt et al., J. Am. Chem. Soc. 113:6634–39, 1991; J. R. Piper et al., J. Med. Chem. 39:1271–80, 1996; B. I. Schweitzer et al., FASEB. 4:2441–52, 1990; J. K. Seydel, J. Chemother. 5:422–29, 1993), and particularly with regard to mycobacteria (K. H. Czaplinski et al., Eur. J. Med. Chem. 30:779–87, 1995; M. Kansy et al., Eur. J. Med. Chem. 27:237–44, 1992; H. H. Locher et al., Antimicrob. Agents Chemother. 40:1376–81, 1996; S. C. C. Meyer et al., Antjiicro. Agents Chemother. 39:1862–63, 1995; R. L. Then, J. Chemother. 5:361–68, 1993). A unique feature of DHFR is the selectivity possible in the design of inhibitors for this target, thus making it an ideal target for antimycobacterial agents using rational and effective drug design. Although genes for DHFR (fol A) have been identified in other bacteria, they are not equivalent to the fol A gene from *M. avium* or other mycobacteria. The enzyme product of the *M. avium* gene (i.e. DHFR) is structurally different from other known DHFRs. For these reasons and others having to do with, for example, toxicity, selective drugs can be designed for individual species. Thus, a selective drug for *M. avium* can be designed in such a way that it will not affect DHFRs in other species, such as humans. One example of the species specific nature of the enzyme is demonstrated by the fact that the diaminopyrinidines, when properly substituted, can be several thousand times more active against bacterial than mammalian DHFR (P. G. Hartran, J. Chemother. 5:369–76, 1993). In addition, there are many possible inhibitors of this enzyme that have not been synthesized or studied (K. Bowden et al., J. Chemother. 5:377–88, 1993). DHFR also represents an enzyme that has been extensively used in the development of site directed inhibitors based upon X-ray crystallographic and molecular graphic studies (K. Bowden et al., J. Chemother. 5:377–388, 1993; M. P. Bradley, J. Med. Chem. 36:3171–77, 1993; B. J. Denny et al., J. Med. Chem. 35:2315–20, 1992; M. McCourt et al., J. Am. Chem. Soc. 113:6634–39, 1991; B. Roth, FASEB. 45:2765–72, 1986; W. M. Southerland, J. Computer-Aided Molecular Design. 8:113–22, 1994).

An important objective in the future development of DHFR inhibitors will be improving delivery of antimycobacterial drugs. One research program, designed to develop sustained and targeted delivery of first-line antituberculosis drugs using micro-encapsulation techniques has successfully formulated a micro-encapsulated form of rifampicin that shows good release characteristics (W. W. Barrow et al., European Society for Mycobacteriology, Institute Pasteur, Paris, France: 1996:50). Use of this formulation has resulted in reduction in colony forming units (CFUs) in both the *M. tuberculosis* H37Rv infected macrophage and mouse models, suggesting that this technology can also be used for other antimycobacterial drugs including the lipophilic DHFR inhibitors.

The history of the development of antifolates is long and includes significant contributions to that area of anticancer and anti-infective drug discovery. Improved agents against opportunistic infections have recently been developed including a synthetic process to prepare 5-alkyl-5-deaza analogs of antifolates, both classical and the lipophilic types. These analogs have been used in several studies (J. R. Piper et al., J. Med. Chem. 39:1271–80, 1996).

Mycobacterial DHFR has been a target for drug design for about three decades. Two groups in particular have synthesized lipophilic antifolates targeting this enzyme in mycobacteria. One group published activity results on a small number of 2,4-diamino-6-substituted pteridines, 6-substituted 8-deazapteridine, 5,6-substituted-5-deazapteridines and 5-methyl-6-substituted-5,8-dideazapteridines (quinazolines) against *M. species* 607 (W. T. Colwell et al., Chemistry and Biology of Pteridines. vol. Elsevier North Holland, Inc., Amsterdam. 215–18, 1979; J. I. DeGraw et al., J. Medicinal Chem. 17:144–46, 1974; J. I. DeGraw et al., J. Medicinal Chem. 17:762–64, 1974). Another group published several papers describing the design and synthesis of substituted 2,4-dianino-5-benzyl pyrimidines (Trimethoprim analogs) active against mycobacterial DHFR from *M. lufu* and screened in vitro against *M. lufu, M. tuberculosis* and *M. marinum* (K. H. Czaplinski et al., Eur. J. Med. Chem. 30:779–87, 1995; M. Kansy et al., Eur. J. Med. Chem. 27:237–44, 1992; J. K. Seydel et al., Chemother. 29:249–61, 1983).

These data support the activity of folate analogs against mycobacteria. Active compounds were obtained in each series of experiments. The quinazoline analogs were targeted as lead compounds. Although quite active against isolated DHFR, these compounds demonstrated poor selectivity. However, it was apparent that selectivity was enhanced by a 5-methyl substitution for both the 5-deaza- and 5,8-di-deazapteridines (quinazolines). Although low toxicity was noted for the quinazolines in mice, equivocal results against *M. leprae* in the mouse foot pad model were noted (W. T. Colwell et al., *Chemistry and Biology of Pteridines*, Elsevier North Holland, Inc., Amsterdam. 215–18, 1979).

One research group has been pursuing trimethoprin analogs such as 2,4-diamino-5-benzylpyrimidine derivatives (M. Kansy et al., Eur. J. Med. Chem. 27:237–44, 1992; J. K. Seydel, J. Chemother. 5:422–29, 1993; J. K. Seydel et al., Chemother. 29:249–61, 1983). Several 4'-modified derivatives have been synthesized to extend into the glutamate binding region of the enzyme (L. F. Kuyper et al., J. Med. Chem. 28:303–11, 1985). A small number of these compounds showed very good selective activity against *M. lufu* in vitro and against the isolated bacterial DHFR (K. H. Czaplinski, Eur. J. Med. Chem. 30:779–87, 1995). The compounds showed an activity profile against *M. tuberculosis* in vitro (M. Kansy et al., Eur. J. Med. Chem. 27:237–44, 1992).

The efficacy of using antifolates against *M. avium* and other mycobacteria has not yet been fully determined. In addition, as new antifolates are developed, their efficacy against *M. avium* and other mycobacteria will need to be evaluated. Such studies could be greatly facilitated through the use of purified recombinant mycobacterial DHFR.

Thus far, there has not been complete or accurate identification, sequencing and cloning of the mycobacterial DHFR gene of any species. Two papers have been published about mycobacterial DHFR. Al-Rubeai et al. (M. Al-Rubeai et al., Biochem. J. 235:301–3, 1986), reported on the purification and characterization of DHFR from *M. phlei* and Sirawarapom et al. (W. Sirawaraporn et al., Exper. Parisitol. 72:184–90, 1991), reported on the purification and characterization of DHFR from a strain of *M. smegmatis*. The reported molecular weights were 15 and 23 kDa for *M. phlei*, and *M. smegmatis* DHFR, respectively. In Sirawaraporn et al., the authors reported on the amino terminal sequencing of the protein. Of the fifteen assignments reported, twelve were stated to be clear, one ambiguous and two could not be determined. Other than this incomplete and partial sequencing of *M. segmatis* DHFR protein, no mycobacterial DHFR DNA sequences have previously been reported.

SUMMARY OF THE INVENTION

The invention is directed to all or portions of novel recombinant nucleic acids encoding, in whole or in part, a dihydrofolate reductase (DHFR) peptide from mycobacteria such as *M. avium* or *M. tuberculosis*, to novel recombinant DHFR peptides produced by such sequences, and to vaccines, diagnostic kits, cells and therapies utilizing these peptides and nucleic acid sequences. The invention is also directed to methods for using the sequences to develop drugs specific to *M. avium* and other mycobacteria, to identify and sequence corresponding sequences in other species of Mycobacterium, as well as to diagnostic and treatment methods incorporating the disclosed sequences and peptides.

One embodiment of the invention is directed to recombinant nucleic acids comprising all or a portion of the nucleic acid sequence that encodes a mycobacterial DHFR protein, such as the DHFR protein of *Mycobacterium avium, Mycobacterium bovis, Mycobacterium tuberculosis* or *Mycobacterium leprae*. The nucleic acid may comprise DNA, RNA or PNA, and may include additional sequences to direct transcription or translation, such as a promoter, a polymerase binding site, an enhancer, or a transcription or translation termination site. The nucleic acid may encode portions of the DHFR protein, such as an enzymatically active portion or antigenically active portion. Alternatively, the sequence may encode the entire amino acid sequence of the DHFR protein.

Another embodiment of the invention is directed to vectors comprising one of these recombinant nucleic acids, or a recombinant cell containing one of these nucleic acids. The nucleic acid may be integrated into the cell's genome, or it may be episomal. The cell may be prokaryotic or eukaryotic.

Another embodiment of the invention is directed to recombinant peptides comprising an amino acid sequence containing all or portion of a mycobacterial DHFR protein, such as *M. avium, M. bovis, M. tuberculosis* or *M. leprae* protein. The recombinant peptide may encode only an enzymatically or antigenically active portion of the peptide, or the entire amino acid sequence of the protein.

Another embodiment of the invention is directed to methods for screening for an agent which inhibits the activity of recombinant DHFR. This method comprises determniing the activity of DHFR protein upon incubation with a plurality of agents and selecting the agent that inhibits the activity. The DHFR protein may be derived from *M. avium, M. bovis, M. leprae, M. tuberculosis* or other mycobacteria. The DHFR protein may be an entire DHFR protein or comprise only selected enzymatically active or antigenically active portions thereof. The plurality of agents may be, for example, over $10^2$ different agents, and may be drawn from a collection of related chemical compounds, including chemical modifications of folate, methotrexate, trimethoprin or combinations thereof. The incubation may comprise mixing the DHFR protein with the agents under conditions allowing for molecular interaction, such as binding, inhibition of enzymatic activity or inhibition of immunogenicity. A preferred embodiment of this method includes the steps of selecting a plurality of agents that inhibit the Mycobacterium DHFR protein, determining the molecular conformation of each agent, and identifying a common inhibitory molecular conformation.

Another embodiment of the invention relates to methods for assessing the ability of an agent to inhibit the activity of a DHFR protein comprising the steps of incubating a recombinant mycobacterial DHFR protein with the agent, determining the activity of the incubated DHFR protein, and comparing the activity with the wild-type activity of the protein. In this method, the activity may be enzymatic activity or immunogenic activity. The agent may be incubated by simply mixing the agent with the protein under, for example, physiological conditions. The agent preferably is usefuil for treatment of a mycobacterial infection. The DHFR protein may be a protein produced by a species selected from the group of *M. avium, M. bovis, M. tuberculosis, M. leprae*, or another mycobacteria, such that the agent is specific for treatment of one of these same species.

Another embodiment of the invention is directed to methods for selecting an antimycobacterial agent specific against a mycobacterial infection comprising crystallizing a recombinant Mycobacterium DHFR protein and determining the molecular conformation of the protein, identifying a binding site within the molecular conformation, and selecting the agent with the molecular structure that fits the binding site. The binding site is preferably a substrate binding site.

Another embodiment of the invention is directed to methods for identifying the sequence of a mycobacterial DHFR gene comprising amplifying nucleic acid in a biological sample containing Mycobacterium by a polymerase chain reaction with two probes which span all or part of the *M. avium* DHFR gene, and determining the sequence of the amplified nucleic acid to identify the sequence of the mycobacterial DHFR gene. Preferably, the sequence identified encodes the DHFR protein of *M. avium, M. bovis, M. tuberculosis* or *M. leprae*. In a preferred embodiment, the sequence of the first probe contains a sequence from the 5' terminus of the *M. avium* gene and the sequence of the second probe contains a sequence from the 3' terminus of the *M. avium* gene.

Another embodiment is directed to methods for detecting Mycobacterium infection such as infection with *M. avium, M. bovis, M. tuberculosis* or *M. leprae*, by contacting a biological sample obtained from a patient with an antibody specific to a recombinant Mycobacterium protein, and detecting bound antibody in the sample. The biological sample may be a sample of bodily fluid from a human. The antibody may be a monoclonal or polyclonal antibody.

Another embodiment of the invention is directed to methods for detecting a Mycobacterium infection by contacting a biological sample obtained from a patient with a recombinant mycobacterial protein or an active portion thereof, and detecting protein bound with antibody from the patient in the sample. The infection may be an infection of *M. avium, M. bovis, M. tuberculosis* or *M. leprae*. In this embodiment, the protein may be labeled with a detectable label, such as a radioisotope, stable isotope, fluorescent chemical moiety, enzyme, metal or combinations thereof.

Another embodiment of the invention is directed to methods for detecting a mycobacterial infection comprising amplifying nucleic acid in a biological sample containing Mycobacterium by a polymerase chain reaction comprising two probes, wherein the two probes span all or part of the *M. avium* DHFR gene, and detecting amplified nucleic acid that corresponds to an amplification of the nucleic acid between the two probes. In a preferred embodiment, the sequence of the first probe contains a sequence from a terminus of the *M. avium* gene and the sequence of the second probe contains a sequence from the opposite terminus of the *M. avium* gene. The two probes may be labeled with detectable labels, such as radioisotopes, stable isotopes, fluorescent chemical moieties enzymes, metals and combinations thereof. In one embodiment, the step of detecting comprises determining the size of the nucleic acid amplified.

Another embodiment of the invention is directed to methods for screening for an agent that interacts with *M. avium* DHFR protein by immunizing an animal with a protein containing at least a portion of the *M. avium* DHFR protein to generate anti-protein antibodies, immunizing another animal with the anti-protein antibodies to generate a collection of anti-idiotypic antibodies, selecting a anti-idiotypic antibody of the collection that binds to dihydrofolate, and identifying an agent that binds to said anti-idiotypic antibody. In this embodiment, the portion of the protein may be an enzymatically active or antigenically active portion, or a conserved region of the DHFR protein. The anti-idiotypic antibody may have an affinity for dihydrofolate that is comparable to the affinity of the catalytic site of *M. avium*

DHFR for dihydrofolate. Preferably, the portion is a peptide corresponding to a region of mycobacterial DHFR protein that is not present in mammalian DHFR protein.

Another embodiment of the invention is directed to methods for detecting *M. avium* in a sample comprising immunizing an animal with a protein containing the DHFR sequence of the present invention to generate antibodies specific to the sequence, immunizing another animal with the antibodies to generate anti-idiotypic antibodies, and detecting *M. avium* DHFR protein in an immunoassay containing said anti-idiotypic antibodies. In this embodiment, the immunoassay may be a competitive immunoassay, an indirect immunofluorescence assay, an ELISA assay, an immunoprecipitation assay or other well-know or useful assay.

Another embodiment of the invention is directed to methods of detecting *M. avium* DHFR in a biological sample comprising the steps of combining a portion of the sample with an idiotypic antibody to *M. avium* DHFR protein, an anti-idiotypic monoclonal antibody to the idiotypic antibody such that the anti-idiotypic monoclonal antibody exhibits structural congruence with at least one epitope of the protein to form an assay mixture in which there is competition between the protein and the anti-idiotypic monoclonal antibody for binding to the anti-idiotypic antibody, and detecting *M. avium*DHFR protein in the sample by determining the amount of bound labeled antibodies disposed within the anti-idiotypic antibody pairs. In one embodiment, determination of the amount of bound labeled antibody disposed within the anti-idiotypic antibody pairs follows a separation of the anti-idiotypic pairs from unbound antibody. Such separation may be achieved by precipitation. In one embodiment, at least one component of the mixture may be labeled with a detectable label, such as a fluorophore, radioactive compound, chemiluminescent compound, latex bead, enzyme, enzyme cofactor or enzyme inhibitor. The idiotypic antibody may be attached to a substrate or, alternatively, the anti-idiotypic antibody may be attached to a substrate.

Another embodiment of the invention is directed to antibodies specifically reactive against DHFR peptides of the invention. Antibodies may be polyclonal or monoclonal and expressed from a population of hybridoma cells. Such antibodies may be reactive against specific epitopes of the peptide such as the substrate binding site.

Another embodiment of the invention is directed to vaccines and diagnostic kits incorporating recombinant Mycobacterium DHFR peptides or antibodies specifically reactive against these recombinant peptides and to methods for using such vaccines and diagnostic kits.

Other embodiments and advantages of the invention are set forth, in part, in the description which follows, and, in part, will be obvious from this description and may be learned from the practice of the invention.

DESCRIPTION OF THE DRAWINGS

FIG. 7 Sequence of *M. avium* DHFR gene (SEQ ID NO 1) and protein (SEQ ID NO 2).

FIG. 9 Alignment of *M. avium* deduced N-terninal peptide sequence (SEQ ID NO 4) with *M. smegmatis* N-terminal peptide sequence (SEQ ID NO 4) previously reported by Sirawarapom et al.

DESCRIPTION OF THE INVENTION

Figure 1:
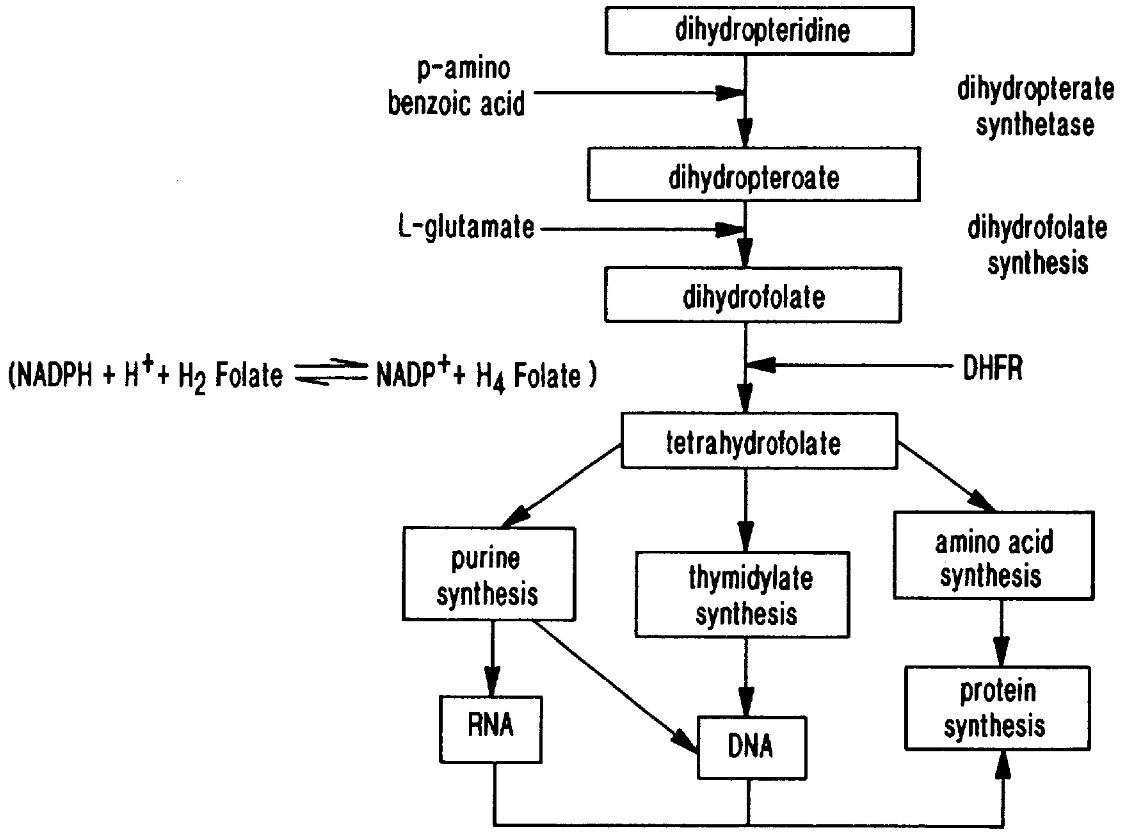
FIG. 1 Block diagram of DHFR's role in biosynthesis of tetrahydrofolate and cell metabolism.

As embodied and broadly described herein, the present invention is directed to novel recombinant nucleic acids encoding DHFR for mycobacteria such as, for example, *M. avium*, to novel recombinant DHFR peptides produced by such sequences, and to vaccines, diagnostic kits, cells and therapies utilizing these peptides and nucleic acid sequences. The present invention is also directed to methods for using the sequences of the present invention to develop drugs specific to *M. avium* and other mycobacteria, to identify and sequence corresponding sequences in species other than *M. avium*, as well as diagnostic and treatment methods incorporating the disclosed sequences and peptides.

In addition to uses relating to *M. avium, M. tuberculosis, M. bovis* and *M. leprae*, the nucleic acid sequences and peptides of the present invention may be useful in sequencing, treatments and diagnostic strategies relating to all species of mycobacteria. These include, but are not limited to, *M. fortuitum* (associated with mastitis in cows, and pulmonary infections, lymph node and cutaneous lesions in animals), *M. chelonei* (associated with contaminated wounds and injection abscesses), *M. marinum* (a human and cold-blooded animal pathogen), *M. scrofulaceum, M. xenopi*, and *M. lepraemurium* (leprosy-like pathogen of cats and rats).

Prior to the present invention, a DHFR gene had not been identified or cloned from any mycobacterial species. However, DHFR genes from other organisms are known. FIG. 9 depicts alignment of the *M. avium* deduced N-terminal peptide sequence of the present invention with the *M. smegmatis* N-terminal peptide sequence reported by Sirawaraporn et al. (W. Sirawaraporn et al., Exper. Parisitol. 72:184–190, 1991). Letters connected with vertical line (|) indicate identical amino acid residues; question marks (?) could not be determined, and letters connected by a point (•) indicate conserved residues. Letters underlined and in italics indicate ambiguous residues. As depicted in FIG. 9, comparison of the deduced N-terminal peptide sequence of the *M. avium* DHFR of the present invention with that of the *M. smegmatis* DHFR reported by Sirawaraporn, et al., revealed that six of the fifteen residues were identical and three were conserved amino acids.

A fol A locus is listed in the GenBank as a putative dihydrofolate reductase gene for *M. tuberculosis* (GenBank Accession No. X59271). However, this gene sequence was not accurately identified. The listed sequence was compared with sixteen other known DHFR gene sequences in the GenBank. The reported sequence for fol A was not significantly homologous with any of the DHFR sequences and it lacked homology with important binding sites for the cofactor NADPH, and the inhibitors trimethoprim and methotrexate. Using primers homologous to the 5' and 3' ends of the putative gene sequence, this presumptive fol A gene was recloned by PCR and expressed in an *E. coli* expression system. The recombinant protein was purified by using a His/tag fusion protein and found to have a molecular weight of about 22 kDa by SDS PAGE. This is close to other DHFR proteins, examples being that from *M. smegmatis* (23 kDa) (W. Sirawarapom et al., Exper. Parasitol. 72:184–90, 1991) and *Staphylococcus haemolyticus* (20 kDa) (G. E. Dale et al., Antimicrob. Agents Chemother. 39:1920–24, 1995). However, the expression vector with the presumptive *M. tuberculosis* GenBank fol A did not complement the DHFR deficient *E. coli* strain D3-157. As a result of these findings, the source for Accession No. X59271 was contacted. It was determined that indeed the sequence of Accession No. X59271 was not the fol A gene and that subsequent work had not been performed to identify the sequence further. Therefore, it appears that a complete DHFR gene has not previously been accurately identified in mycobacteria, cloned in any system or expressed.

Figure 2:
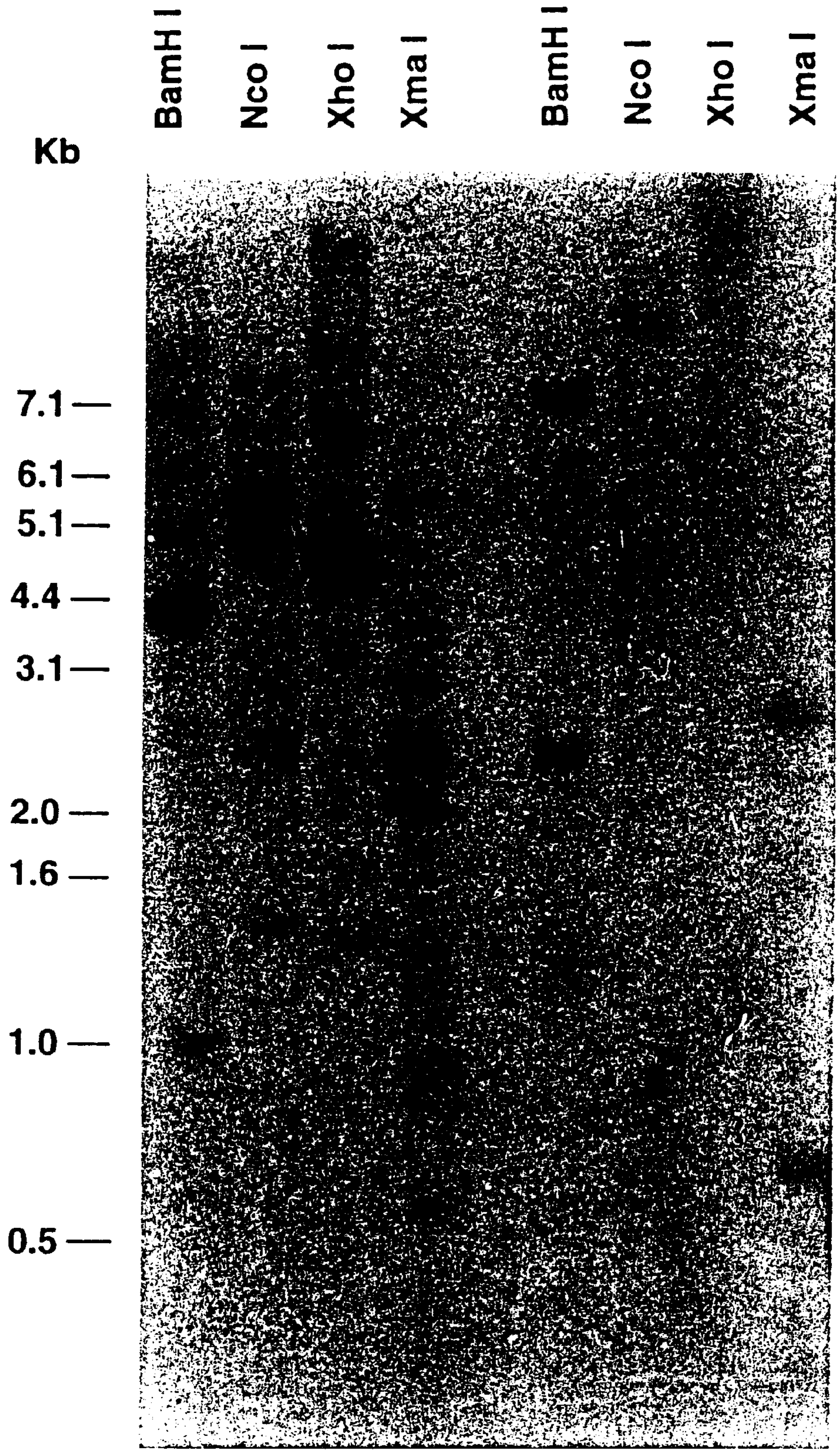
FIG. 2 Autoradiogram of Southern blot of genomic DNA from (A) *M. tuberculosis* H37Ra and (B) *M. avium* serovar 4.

Next, both the *M. avium* and *M. tuberculosis* genormic libraries were screened with a probe made from the DHFR gene of *Pneumocystis carinii*. No clones that would hybridize with this probe were identified from either library. Two optimized oligo probes were made from the binding sites of trimethoprim, methotrexate, and the cofactor NADPH on the *P. carinii* DHFR gene using the aligned sequences of 16 species as a guide to the homologous regions (G. E. Dale et al., Antimicrob. Agents Chemother. 39:1920–24, 1995). These probes were used in a Southern blot reaction with genomic DNA from *M. avium* (serovar 4) and *M. tuberculosis* H37Ra, digested with several restriction enzymes. FIG. 2 depicts an Autoradiogram of a Southern blot of genomic DNA from (A) *M. tuberculosis* H37Ra and (B) *M. avium* serovar 4. As indicated by FIG. 2, both probes hybridized to the genomic DNA of both species, indicating homologous regions.

The functional recombinant *M. avium* DHFR gene has now been successfully cloned via genetic complementation and expressed as an active protein in *E. coli*. FIG. 7 depicts the sequence of this cloned *M. avium* gene (SEQ ID NO 1) with flanking 5' and 3' regions obtained by automated DNA sequencing. The open reading frame is in bold (nucleotide 57 to 559). The polypeptide sequence (single letter code) of the open reading frame is indicated below the DNA sequence in capital letters. The methionine initiation codon used by *M. avium* is indicated by 'M' at position 57 (ATCC Accession No. AF006616).

As shown in FIG. 7, the *M. avium* DHFR gene has an open reading frame of 543 bp and contains a guanosine plus cytosine content of 73%, consistent with other mycobacterial DNA. The translated polypeptide sequence of the *M. avium* gene compares favorably with that of other bacterial DHFRs, showing 58% identity to the consensus sequence of the conserved regions from eight other bacterial DHFRs. The recombinant *M. avium* DHFR was expressed actively in *Escherichia coli*. SDS PAGE analysis of recombinant DHFR protein revealed a 20 kDa species, agreeable with that predicted from the polypeptide sequence.

Figure 6:
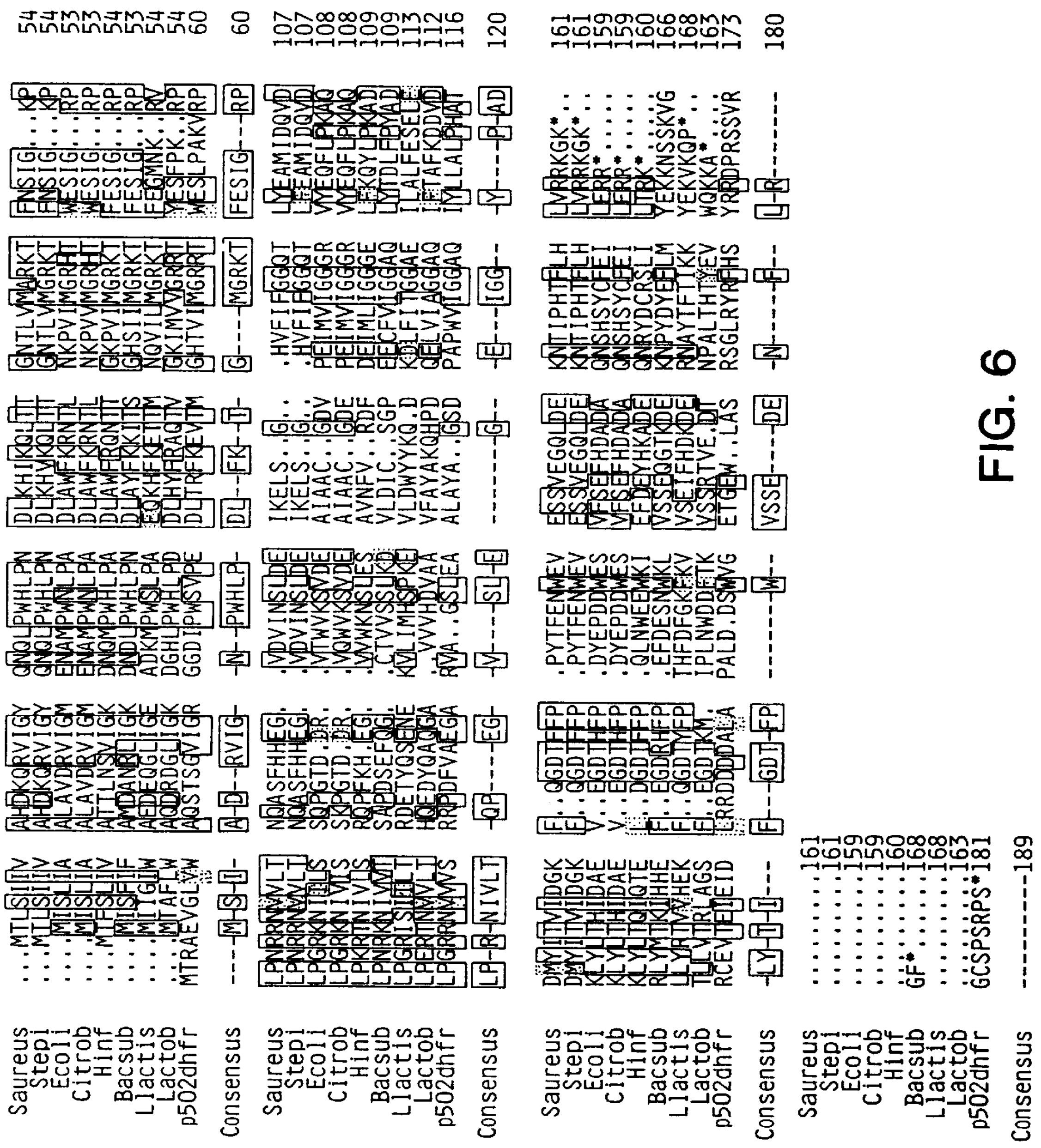
FIG. 6 Comparison of deduced amino acid translation of the p502 DHFR clone from *M. avium* (Consensus SEQ ID NO 2) with the deduced amino acid translation DHFR sequences from other prokaryotic DHFR sequences from the GenBank (Stepi SEQ ID NO 5; Ecoli SEQ ID NO 6; Citrob SEQ ID NO 7; Hinf SEQ ID NO 8; Bacsub SEQ ID NO 9; Llactis SEQ ID NO 10; Lactob SEQ ID NO 11; P502dhfr).

FIG. 6 depicts a comparison of the deduced amino acid translation of the p502 DHFR clone from *M. avium* with the deduced amino acid translation DHFR sequences from other prokaryotic DHFR sequences from the GenBank, namely: *Staphylococcus aureus* (Saureus); *Staphylococcus epidermidis* (Stepi); *Escherichia coli* (Ecoli); *Citrobacter freundii* (Citrob); *Haemophilus influenzae* (Hinf); *Bacillus subtilis* (Bacsub); *Lactococcus lactis* (Llactis); *Lactobacillus casei* (Lactob). Analysis of predicted amino acid sequences were performed using Wisconsin Package Version 9.0, Genetics Computer Group (GCG) (Madison, Wis.). Alignments were carried out using TRANSLATE, PILEUP, and PRETTYBOX programs. Black boxes indicate amino acid identity, gray boxes indicate similar amino acids, and dots indicate gaps in the alignment. Following genetic complementation cloning, the open reading frame was found for which the peptide sequence aligns with that of other DHFR genes.

Although the DHFR gene had not previously been cloned from any mycobacterial species, the nucleotide sequence for the DHFR gene has been known for a number of bacterial species. Of the known DHFR genes, the most related species to Mycobacterium are *Staphylococcus aureus, Staphylococcus epidermidis, Bacillus subtilis*and *Lactobacillus casei*. These sequences were used to choose regions of homology between the genes, particularly in the regions involved in the binding of trimethoprim, methotrexate and the cofactor NADPH. These sequences were also used to make probes and PCR primers based on the known nucleotide codon preference of *M. tuberculosis*. Identification and cloning of the DHFR gene in *E. coli* by genetic complementation allows for expression of the gene and gene segments in *M. smegmatis* $MC^2155$, to produce fimctional enzymes and enzyme fragments. Both *M. avium* and *M. tuberculosis* genoric libraries, genomic DNA from both species *M. tuberculosis* H37Ra and *M. avium* serovars 4 and 8, *Escherichia coli* D3-157 deficient in DHFR are available and can be used in complementation experiments, and *M. smegmatis* $MC^2155$ for expression of recombinant DNA.

A comparison of the specific activity of the soluble DHFR protein expressed by p807 with that previously reported for purified mycobacterial DHFR (M. Al-Rubeai et al., Biochem. J. 235:301–3, 1986, W. Sirawarapom et al., Exper. Parisitol. 72:184–90, 1991) indicates that the p807-expressed enzyme represented about 2% of the total soluble protein. In contrast, DHFR, present in endogenous *M. avium* extracts represents about 0.01% of the total soluble protein.

Figure 4:
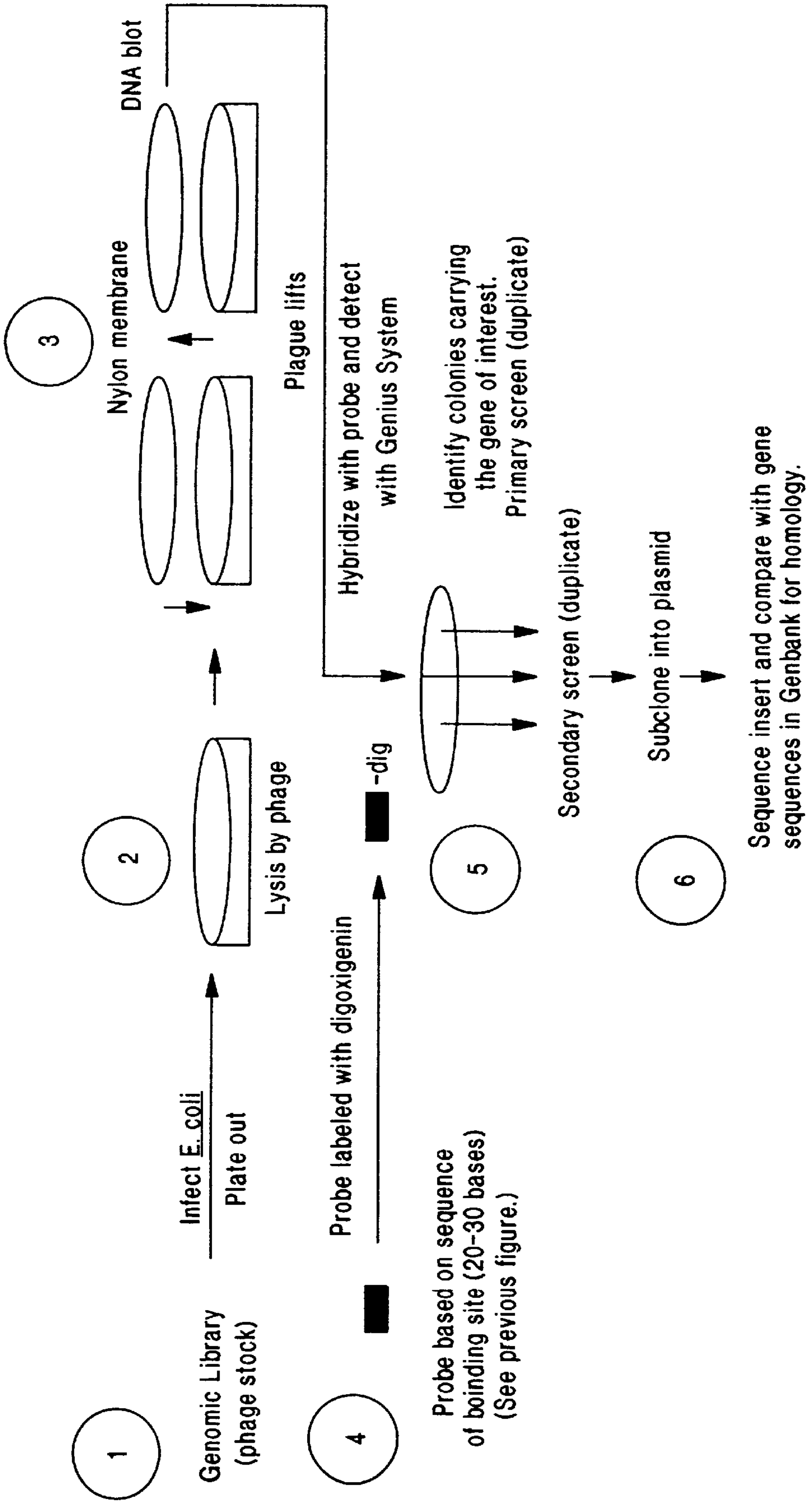
FIG. 4 Flow diagram depicting procedures used for screening genomic libraries for the DHFR gene *M. avium.*
Figure 5:
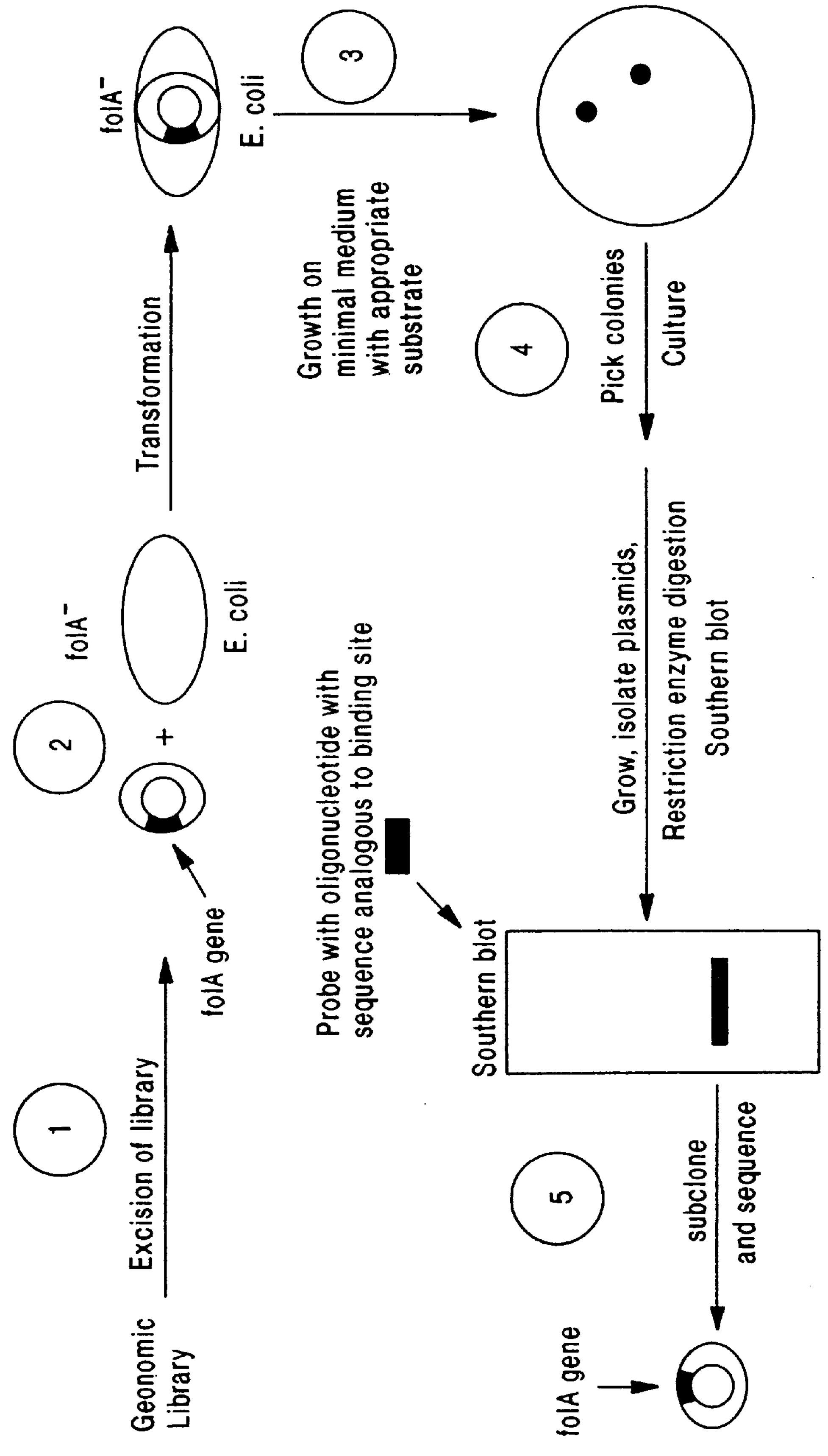
FIG. 5 Flow diagram depicting procedures used for complementation studies and cloning by deduced amino acid sequences.

In addition to genetic complementation, strategies for screening and cloning the DHFR gene from *M. avium* and other mycobacteria such as *M. tuberculosis*, include, for example, use of PCR for cloning from genomic DNA (FIG. 3, Example 9), bacteriophage genomic library screening (FIG. 4, Example 10), and gene cloning by deduced aniino acid sequence (FIG. 5, Example 12). The present invention represents the first report of the cloning, expression, purification and demonstration of biochemical activity of a recombinant mycobacterial DHFR protein.

Based upon experiences with the development of DHFR inhibitors and inhibitor-drug combinations, and experience with Mycobacterium species, the successful cloning of the DHFR gene from *M. avium* and other species now allows for the recombinant proteins to be used, for example, for kinetic analyses and binding studies with drug compounds. DHFR proteins are also useful for obtaining information on molecular structure, including x-ray crystallographic structure and molecular graphics, for drug design and modeling studies.

One embodiment of the invention is directed to the recombinant DHFR nucleic acid of Mycobacterium and, specifically, the *M. avium* DHFR gene sequence (SEQ ID NO 1), as depicted in FIG. 7. This sequence comprises the

*M. avium* DHFR gene with flanking 5' and 3' regions obtained by automated DNA sequencing. The nucleic acid sequence may comprise DNA, RNA or PNA, and may further contain one or more additional sequences to direct transcription or translation of the protein product. These additional sequences may be origins of replication, promoters, polymerase binding sites, enhancers, or transcription or translation termination sites. Such sequences may be homologous to mycobacterial cells or heterologous, selected for a level of expression in a heterologous host cell.

Another embodiment of the invention is directed to a vector, such as prokaryotic, eukaryotic or combination shuttle vectors, or an other suitable vector which contains the nucleic acid sequence of SEQ ID NO 1. Alternatively, the nucleic acid sequence may be integrated into the genome of a recombinant cell, or be contained within a recombinant cell episomally. The recombinant cell may be prokaryotic such as, for example, *E. coli, B. subtilis* or *P. aeruginosa*, or eukaryotic such as, for example, human, primate, rabbit or another mammalian cell. Integration may be performed by transfection, transformation, lipofection or any of the well-known methods of integrating a nucleic acid into a cellular genome. Integrated cells can be maintained in tissue culture or in vivo as desired.

Another embodiment of the invention is directed to a recombinant nucleic acid which contains a nucleic acid sequence encoding at least a portion of the DHFR protein of a Mycobacterium. The portion may be an enzymatically active portion which may be more usefull in certain drug-development procedures. Alternatively, the portion may be an antigenically active portion. The sequence may encode for the entire amino acid sequence of a mycobacterial DHFR protein. The DHFR protein may be derived from *M. avium, M. bovis, M. tuberculosis* or *M. leprae*, or another Mycobacterium species.

Another embodiment of the invention is directed to a recombinant DHFR peptide comprising an amino acid sequence that contains a sequence of mycobacterial DHFR such as, for example, SEQ ID NO 2, or at least a portion of the amino acid sequence of a Mycohacterium DHFR protein. The portion of the recombinant peptide may be an enzymatically active portion, or may be an antigenically active portion. The sequence may also contain the entire amino acid sequence of a DHFR protein of Mycobacterium. This DHFR protein may be derived from any Mycobacteri urm species, including *M. avium, M. bovis, M. tuberculosis*, or *M. leprae*. The DHFR protein may be a purified protein from *M. avium, M. bovis* or *M. tuberculosis*.

Recombinant DHFR peptides of the present invention are useful in the development of anti-infectives. For example, recombinant peptide may be used to screen potentially effective inhibitors of that drug target, determine enzyme kinetics, and to develop more effective and better drugs through molecular modeling and other drug-development techniques, which are well-known to those of ordinary skill in the art.

Recombinant DHFR peptides may also be used as vaccines against or to prevent mycobacterial infections, or diagnostically in a kit. For example, DHFR peptide may be mixed with an appropriate diluent and injected into an animal, person or other host to stimulate a desired immune response. Alternatively, antibodies specifically reactive against the recombinant peptide, such as monoclonal or polyclonal antibodies may be generated, collected and, as necessary or desired, purified by techniques all of which are well-known to those of ordinary skill in the art. Monoclonal antibodies can be purified from cell cultures of hybridoma cells from human, primate or other mammalian cells. The antibody may be, for example, a recombinant such as a humanized antibody. Such antibodies may be used, for example, as a vaccine or in a diagnostic kit.

Another embodiment of the invention is directed to a method for assessing the ability of an agent to inhibit the activity of a DHFR protein. Recombinant DHFR of, for example, *M. avium* or *M. tuberculosis* can be isolated, characterized and used to screen for antimycobacterial agents. It can be used in studies to improve the binding potential of the lipophilic DHFR inhibitors and predict new second generation analogs with improved antimycobacterial activity. The sequence of the DHFR gene of *M. avium, M. tuberculosis* or related species, can be subcloned into appropriate vectors and the DHFR protein expressed to develop site directed lipophilic DHFR inhibitors by means of X-ray crystallographic and other molecular graphic techniques. Specifically, potential lipophilic inhibitors can be synthesized to screen against mycobacterial DHFR in vitro. In the absence of a 3-dimensional enzyme structure from X-ray diffraction, the in vitro mycobacterial DHFR data for these lipophilic antifolates can be used to carry out a comparative molecular field analysis (CoMFA) (K. H. Czaplinski, Eur. J. Med. Chem. 30:779–87, 1995). This analysis can be used to relate activity to specific molecular properties and shapes in order to predict newer, second generation analogs with improved activity as part of an iterative drug-design process.

In addition to using recombinant *M. avium* DHFR to develop new drugs, existing anti-DHFR analogs can be screened using the DHFR protein for inhibition activity. Further, the disclosed sequence of the present invention can be used to identify corresponding genes in other mycobacterial species, and to identify other genes coding for enzymes important in folic acid synthesis. This information can then be used to develop drugs that inhibit enzymes in the same pathway as DHFR. Such drugs may be used in combination with anti-DHFR drugs to increase the therapeutic advantage of such a treatment strategy.

Another method comprises incubating a recombinant mycobacterial DHFR protein with the agent, determining the activity of the incubated DHFR protein, and comparing the activity determined with the wild-type activity of the protein. The activity inhibited may be enzymatic activity, immunogenicity or another activity. The step of incubating may comprise mixing the agent with the protein under physiological conditions such as physiological temperature or lower (room temperature; about 22° C.), physiological pH (e.g. about 7.2), and physiological ionic conditions (e.g. 0.9% NaCl or PBS). In a preferred embodiment, the agent selected is useful for the treatment of any mycobacterial infection. The Mycobacterium DHFR protein may be of a specific species selected from the group consisting of *M. avium, M. bovis, M. tuberculosis, M. leprae* or another Mycobacterium species, such that the agent is specific for treatment caused by only that species of a selected group of species.

Other embodiments of the invention are directed to methods of identifying and screening agents suitable for inhibiting the activity of mycobacterial DHFR. One method of screening for an agent that inhibits the activity of recombinant DHFR protein of a Mycobacterium comprises the steps of determining the activity of the DHFR protein upon incubation with each of a plurality of agents, and selecting the agent that inhibits DHFR protein activity. The agent may inhibit all mycobacterial species, or may selectively inhibit *M. avium, M. bovis, M. tuberculosis, M. leprae*, or others.

The DHFR protein may contain the sequence of SEQ ID NO 2, or an active portion thereof. This active portion may be an enzymatically active portion or an antigenically active portion. Through the use of high through-put screening, a large number of agents can be screened, such as greater than $10^2$ different agents, preferably greater than $10^4$, more preferably greater than $10^6$, or greater than about $10^8$, or more. These agents may comprise a collection of related chemical compounds such as, for example, chemical modifications of folate, methotrexate, trimethoprin, quinazoline or combinations of these agents, or combinantions of these agents with other anti-mycobacterial agents such as, for example, rifampicin, streptomycin and isoniazid.

The step of incubation may comprise mixing the DHFR protein with the agent under conditions well-known to those of ordinary skill in the art that allow for molecular interaction to occur. The desired molecular interaction may be binding, or inhibition of activity such as enzymatic activity. Alternatively, the activity inhibited may be immunoginecity. Additionally, the method may further comprise the step of determining the molecular conformation of said agent again using techniques well-known to those of ordinary skill in the art such as, for example, a comparative molecular field analysis (CoMFA).

This method may further comprise the steps of selecting a plurality of agents that inhibit the activity of the Mycobacterium DHFR protein, determining the molecular conformation of each agent selected, and identifying a common inhibitory molecular conformation. For example, in many cases, agents tested may have a known or easily determinable molecular conformation. Identification of a common structure or sub-structure within that conformation usinf, for example, well-known crystallographic techniques or structure-activity relationships learned from folate gene products, allows one of ordinary skill in the art to design and construct more effective agents.

Use of Mycobacterium DHFR protein to identify useful antimycobacterial drugs has several advantages. Looking at inhibition of enzyme rather than inhibition of growth of viable microorganisms is faster, less hazardous, less expensive and poses fewer complications. In addition, using the DHFR protein itself to identify inhibitors of Mycobacterium DHFR allows for more direct evaluation of efficacy and facilitates additional drug discovery.

To discover antimycobacterial drugs, in the absence of an actual X-ray structure, computer modeling may be used to obtain a 3-dimensional picture of the recombinant *M. avium* DHFR active site and correlate structural alterations with differences in pharmacologic activity. The success of this approach can depend on how robustly a CoMFA performs. The quality of the analysis and subsequent predictions are directly correlated to the quality and number of components that are analyzed. A CoMFA has been published using 14 Trimethoprim analogs against DHFR from various species including *M. lufu* (K. H. Czaplinski, Eur. J. Med. Chem. 30:779–87, 1995). However, very poor correlation coefficients were obtained for the *M. lufu* analysis. Derivation of structure activity relationships for small data sets non-homogeneous in structure and/or conformation can lead to erroneous results (K. H. Czaplinski, Eur. J. Med. Chem. 30:779–87, 1995). In other CoMFA studies involving enzyme receptors, the use of at least 50 inhibitors has resulted in much better predictive capability (M. A. El-Bermawy et al., Med. Chem. Res. 2:290–97, 1992; C. L. Waller et al., J. Med. Chem. 36:2390–403, 1993; C. L. Waller et al., Chem. Res. Toxic. 8:847–58, 1995). Thus, by using at least 50 structurally similar derivatives, a high quality first model from which to make predictions for second generation compounds to be synthesized can be produced. Further refinement of the model with data from new inhibitors could validate and increase its predictive capability. The recombinant protein could serve as a valuable reagent for these studies to identify new drugs.

In one embodiment, a CoMFA may also be used in connection with a method for selecting an antimycobacterial agent specific against a Mycobacterium infection. This method comprises the steps of crystallizing a recombinant mycobacterial DHFR protein and determining the molecular conformation of the protein, identifying a binding site within the molecular conformation, and selecting the agent with a molecular structure that fits within the binding site. In this method, the binding site may be a substrate binding site. Positron emission topography (PET) can also be used to analyze molecular structure. PET techniques are well know to those of ordinary skill in the art.

Another embodiment of the invention is directed to methods for identifying sequences of mycobacterial DHFR genes. A preferred method comprises amplifying nucleic acid in a biological sample containing Mycobacterium by a polymerase chain reaction with two probes which span the *M. avium* DHFR gene. The sequence of the first probe preferably contains a sequence from the 5' terminus of the *M. avium* gene and the second probe preferably contains a sequence from a 3' terminus of the *M. avium* gene. The method comprises a second step of determining the sequence of the amplified nucleic acid to identify the sequence of the mycobacterial DHFR gene. Sequences identified may encode the DHFR protein of *M. avium, M. bovis, M. tuberculosis, M. leprae* or other mycobacterial species.

In another embodiment, the mycobacterial DHFR gene can be sequenced by contacting geriomic DNA of a target mycobacterial species with a probe containing all or part of SEQ ID NO 1 and identifying hybridized regions of homology between the genomic DNA and the sequence. The *M. avium* sequence utilized may comprise one or more binding sequences, such as the portion of the DHFR protein that binds with trimethoprin, methotrexate, or NADPH. The target DNA may then be isolated and sequenced.

Another embodiment of the invention is directed to a method for detecting a Mycobacterium infection. In this method, a biological sample from a patient is contacted with an antibody specific to a recombinant Mycobacterium protein. Bound antibody is then detected in the sample. The mycobacterial infection may be due to *M. avium, M. bovis, M. tuberculosis, M. leprae*, or other mycobacterial infection. The biological sample may be a sample of bodily fluid or tissue. The patient may be an animal or a human suspected of harboring a mycobacterial infection. The antibody may be a monoclonal antibody, a polyclonal antibody or another type of antibody. Detection can be performed using a wide variety of techniques, all well-known and widely used in the art.

Another embodiment is directed to a method of detecting Mycobacterium infection by contacting a biological sample obtained from a patient with a recombinant mycobacterial protein or active portion thereof, and detecting protein bound with antibody from the patient in the sample. The infection may be due to *M. avium, M. bovis, M. tuberculosis, M. leprae*, or other Mycobacterium. The protein may be labeled with a detectable label such as a radioisotope, stable isotope, fluorescent chemical moiety, enzyme, metal or combination thereof.

Another embodiment of the invention is directed to a method for detecting mycobacterial infection by a first step of amplifying nucleic acid in a biological sample containing Mycobacterium by polymerase chain reaction. This can be accomplished through the use of two probes, wherein the sequences of the two probes span the *M. avium* DHFR gene. The sequence of the first probe preferably contains a sequence from a terminus of DHFR gene and the sequence of the second probe preferably contains a sequence from the opposite terminus of the *M. avium* DHFR gene. The method includes the further step of detecting amplified nucleic acid that corresponds to an amplification of the nucleic acid between the two probes. The two probes may be labeled with detectable labels, such as radioisotopes, stable isotopes, fluorescent chemical moieties, enzymes, metals and combinations thereof. In the step of detecting, the size of the nucleic acid amplified may be determined.

Another embodiment of the invention is directed to an immunoassay for the detection of *M. avium* DHFR. The assay detects *M. avium* DHFR by its inhibition of the reaction between the combining site of an idiotypic antibody to DHFR and an anti-idiotypic antibody. The assay provides a method for measuring the existence and concentrations of single epitopes without requiring purified DHFR or mycobacteria. One advantage of this method is that it can detect unpurified *M. avium* DHFR even in a mixture of antigens. Another advantage of the method is that it provides a consistent, specific reagent for DHFR measurement which is not dependent on the catalytic function of DHFR. A third advantage of the system is that it is more resistant to enzyme inhibitors, detergents and ions than assays based on DHFR enzyme activity.

Another embodiment of the invention is directed to a method to screen for an agent or group of agent which interact with *M. avium* DHFR protein. In this method, an animal is immunized with a protein comprising a sequence that contains, for example, at least a portion of the protein identified in SEQ ID NO 2 to generate anti-protein antibodies, immunizing another animal with the anti-protein antibodies to generate a collection of anti-idiotypic antibodies, selecting an anti-idiotypic antibody of the collection that binds to dihydrofolate, and identifying an agent that binds to the anti-idiotypic antibody. The portion of SEQ ID NO 2 may be an enzymatically active portion, an antigehically active portion, or a conserved region of the DHFR protein. The anti-idiotypic antibody may have an affinity for dihydrofolate that is comparable to the affinity of the catalytic site of *M. avium* DHFR for dihydrofolate. In a preferred embodiment, the portion is a peptide that corresponds to a region of mycobacterial DHFR protein that is not present in mammalian DHFR protein. Such an embodiment allows for treatment of a mammalian patient with an agent which would have an adverse effect on mycobacterial DHFR while sparing the host's DHFR protein.

Another embodiment of the invention is directed to a method for detecting *M. avium* in a sample by immunizing an animal with a protein containing, for example, SEQ ID NO 2 or a portion thereof to generate antibodies specific to the sequence, immuzizing another animal with the antibodies to generate anti-idiotypic antibodies, and detecting a *M. avium* DHFR protein in an immunoassay containing the anti-idiotypic antibodies. In this embodiment, the immunoassay may be a competitive immunoassay, an indirect immunofluorescence assay, an ELISA assay, an irnmunoprecipitation assay, or other assay known in the art.

Another embodiment of the invention is directed to a method for detecting *M. avium* DHFR in a biological sample comprising the steps of combining a portion of the sample with an idiotypic antibody to *M. avium* DHFR protein, an anti-idiotypic monoclonal antibody to the idiotypic antibody wherein the anti-idiotypic monoclonal antibody exhibits structural congruence with at least one epitope of the protein to form an assay mixture in which there is competition between the protein and the anti-idiotypic monoclonal antibody for binding to the anti-idiotypic antibody, and then detecting *M. avium* DHFR protein in the sample by determining the amount of bound labeled antibodies disposed within the anti-idiotypic antibody pairs. In a preferred embodiment, determining the amount of bound labeled antibodies disposed within the anti-idiotypic antibody pairs follows a separation of the anti-idiotypic antibody pairs from unbound antibody. Separation may be by precipitation and at least one component of the mixture may be labeled with a detectable label such as, for example, a fluorophore, radioactive compound, chemiluminescent compound, latex beads, enzyme, enzyme cofactor or enzyme inhibitor. The idiotypic antibody may be attached to a substrate. Alternatively, the anti-idiotypic antibody may be attached to a substrate.

The following examples are offered to illustrate embodiments of the invention, and should not be viewed as limiting the scope of the invention.

EXAMPLES

Example 1

Cloning of DHFR Gene From Mycobacterial Species by Genetic Complementation

At least four independent strategies can be used to screen or clone the DHFR gene from *M. avium* and *M. tuberculosis* H37Ra and other mycobacteria. The four approaches include PCR (FIG. 3), bacteriophage genomic library screening (FIG. 4), genetic complementation (FIG. 5), and gene cloning by deduced amino acid sequence (FIG. 5) As discussed, the *M. avium* fol A gene (DHFR) was first successfully cloned via genetic complementation.

Bacterial Strains. For genetic complementation, a DHFR-deficient *Escherichia coli* strain D3-157 (S. Singer et al., J. Bacteriol. 164:470–72, 1985) was purchased from the American Type Culture Collection (Rockville, Md.). This strain contains a DHFR mutation that maps at or near the fol A gene and was given the designation fol-200 (S. Singer et al., J. Bacteriol. 164:470–72, 1985). Other *E. coli* strains which may be used are JM109 (Promega, Madison, Wis.), for cloning of plasmid constructs, and BL21(DE3)plysS (Novagen, Madison, Wis.), a lysogen of bacteriophage lambda DE3 containing the plasmid plysS, for controlling expression of proteins from the pET-15b vector. Useful bacterial strains and plasmids are listed in Table 1.

TABLE 1

List of *Escherichia coli* strains and plasmids.

| Strain or plasmid | Relevant genotype or properties | Origin |
|---|---|---|
| D3-157 | F—, guaB22, xyl-7, rpsL125, fol - 200, $Strep^r$ | ATCC |
| JM109 | endA1, recA1, gyrA96, thi, hsdR17, ($r_k^-$, $m_k^+$), relA 1, $supE^{44}$, λ-, Δ (lac-pro AB), [F—, traD36, proAB, lac $1^q$ZΔM15] | Promega |

TABLE 1-continued

List of *Escherichia coli* strains and plasmids.

| Strain or plasmid | Relevant genotype or properties | Origin |
|---|---|---|
| BL21(DE3)plysS | F—, ompT, hsd $S_B$ ($r_{B-}m_{B-}$), gal, dcm, (DE3)plysS | Novagen |
| pBS+ | $Amp^r$, lac Z, promoter | Stratagene |
| pGEM ®-7Zf+ | $Amp^r$, T7 and SP6 promoters | Promega |
| pGEM ®-T Easy | $Amp^r$, T7 and SP6 promoters | Promega |
| pET-15b | $Amp^r$, T7 lac promoter, His · Tag fusion protein | Novagen |
| p502 | $pBS^+$with *M. avium* genomic DNA insert | This study |
| p807 | pET-15b with *M. avium* folA gene inserted in frame with T7 lac promoter | This study |

Screening of genomic DNA library by complementation. An *M. avium* genomic DNA library in the λ ZAPII vector (Stratagene, La Jolla, Calif.) was obtained through the AIDS Research and Reference Reagent Program, Division of AIDS, NIAID, NIH (Catalog Number 1786, contributed by BioTechnology General). The vector was excised with helper phage and recircularized according to the manufacturer's protocol to make subclones in the pBluescript® (pBS+) vector which represented the genomic DNA fragments from $10^6$ pfu of the phage library. The plasmid genomic library (P502) was then purified twice with a CsCl gradient. A 100 ng aliquot of the plasmid genomic library was transformed into the DHFR deficient *E. coli* strain D3-157 and plated onto M9 minimal salts medium lacking thymidine (J. Sambrook et al., *Molecular Cloning: a Laboratory Manual*, second ed., New York: Cold Spring Harbor Laboratory Press, 1989) supplemented with tryptophan, tyrosine, and histidine (50 μg/ml), guanine (20 μg/ml), thiamine (10 μg/ml), streptomycin and ampicillin (100 μg/ml), and IPTG (1 mM).

The *M. avium* genomic library successfully complemented the *E. coli* DHFR deficient strain, D3-157, using described methods (G. Vasanthakumar et al., Gene 147:153–54, 1994). One concern with this approach was that the Mycobacterium promotor might not be recognized by the *E. coli* host cell; however, it was expected that some of the genomic DNA constructs would contain the DHFR gene in close enough proximity to the *E. coil* plasmid promotor to utilize it in making DHFR to complement the deficient strain. The deficient *E. coil* strain D3-157 was transformed with the *M. avium* genomic library, as described above, and plated onto minimal media supplemented with D3-157 strain nutritional requirements except thymidine. After the plates were incubated at 37° C. for five days, four colonies were seen, indicating successful complementation and functional expression of the *M. avium* gene insert.

The deficient strain should be complemented by any *M. avium* plasmid from the genomic library that expresses the DHFR gene, such as the above described plasmid clone P502.

Example 2

Southern Blot Analysis

Plasmids from the *M. avium* library clones of Example 1 were purified by CsCl gradient centrifugation. Positive clones were verified by Southern blotting and subjected to DNA sequencing. Restriction enzyme digests and Southern blots were done according to standard protocol (J. Sambrook et al., *Molecular Cloning: a Laboratory Manual*, second ed., New York: Cold Spring Harbor Laboratory Press, 1989). The oligonucleotide probe (5'-AATGCCGTGATGATGGGCCGGAAGACCTGGGAATCGAT-3' SEQ ID NO 12), which was prepared by Genosys (The Woodlands, Tex.), was 3'-end labeled with digoxigen-11-ddUTP and hybridization was performed with the Genius™ system according to the manufacturers' specifications (Boehringer Mannheim, Indianapolis, Ind.).

Restriction enzyme digestion of p502, a plasmid isolated from one of the complementation colonies, revealed a 6.4 kb insert of genomic DNA. To identify the DHFR gene, the 38 base oligonucleotide probe described above was made based on the aligned sequences of the methotrexate binding sites of known DHFR genes from other species and the codon preferences of Mycobacterium (S. G. E. Anderson et al., Microbiol. 142:915–25, 1996). The complementation plasmid insert was cut with Bam, HI, Xho I, Apa I, and Hin dIII, and then hybridized in a Southern blot. The probe hybridized to the 1.6 kb Apa I fragment which was subsequently cloned into the Apa I site of pGEM®-7Zf+ (Promega, Madison, Wis.).

Example 3

DNA Sequencing and Analysis

The DNA sequencing was determined by dideoxy chain termination method using the ABI PRISM™ Dye Terminator Cycle Sequencing kit (Perkin-Elmer; Foster City, Calif.) and the ABI PRISM™ 377 automated DNA Sequencer, either in house or through the DNA Sequencing Facility at Iowa State University, Ames, Iowa. Primers used for sequencing were made by Gibco BRL (Gaithersburg, Md.). The DNA sequence encoding the *M. avium* fol A gene was submitted to GenBank and assigned to the Accession No. AF006616.

Analysis of nucleotide and predicted peptide sequences was performed using the Wisconsin Package Version 9.0, Genetics Computer Group (GCG) Madison, Wis.) (J. Devereux et al., Nucleic Acids Res. 12:387–95, 1984). Alignments were carried out using TRANSLATE, PILEUP and PRETTYBOX programs.

The 1.6 kb subclone of the p502 complementation plasmid was sequenced and an open reading frame (ORF) was found (FIG. 7). A deduced polypeptide sequence comparison with other DHFR genes indicated that a portion of the 5' end of the gene was not in the 1.6 kb insert. Therefore, the sequence of the entire gene was determined from both strands of p502. The nucleotide sequence of the *M. avium* fol A gene is given in FIG. 7, along with the translated amino acid sequence. The open reading frame is 543 bp in length and has a guanosine plus cytosine (G/C) content of 73%, in agreement with that found for most mycobacterial DNA (S. G. E. Anderson et al., Microbiol. 142:915–25, 1996; J. E. Clark-Curtiss, *Molecular Biology of the Mycobacteria*, 77–96, 1990).

The translated polypeptide sequence from the *M. avium* fol A gene was aligned with those of several other known bacterial DHFR genes, including *Staphylococcus aureus, Staphylococcus epidermidis, E. coli, Citrobacter freundii, Haemophilus influenzae, Bacillus subtilis, Lactoccus lactis*, and *Lactobacillus casei* (FIG. 6). Comparison of the polypeptide sequence of the *M. avium* fol A gene with that from eight other bacterial DHFR genes revealed a 58% identity to the consensus sequence derived from the conserved regions of the bacterial genes.

In a Southern hybridization, the probe BSDHFR was found to hybridize strongly with p502 DNA. A 1.6 kb restriction enzyme digested fragment from the 6.4 kb *Mycobacterium avium* genomic DNA insert from p502 that also hybridized with the BSDHFR probe was subcloned, p502-7, and partially sequenced. Within this clone, p502-7, a region was found that contained an open reading frame that was homologous to DHFR genes from other species and contained the binding sites for the cofactor NADPH, and the inhibitors trimethoprim and methotrexate.

Example 4

Construction of Expression Plasmid

PCR may performed with oligonucleotide primers (GIBCO BRL; Gaithersburg, Md.), using Taq DNA polymerase (Fisher Scientific; Pittsburgh, Pa.) according to manufacturer specifications except that dimethyl sulfoxide may be added to the reaction at a final concentration of 5%. Primers, are 8DHFR, 5'-CATATGACCCGTGCCGAGGTG-3' (SEQ ID NO 13) and 7DHFR, 5'-GGATCCTCAGCTCGGGCGTGAGG-3' (SEQ ID NO 14), include Nde I and Bam HI restriction enzymes sites to the 5' and 3' ends of the fol A gene respectively. The template DNA is denatured at 95° C. for 3 minutes and PCR is performed for 35 cycles of 95° C. for 1 minute, 60° C. for 1 minute, and 72° C. for 1 minute with a 7 minute extension cycle at 72° C. PCR product is isolated in a 0.8% agarose gel and the DNA eluted from the gel slice by centrifugation with an Ultrafree™-MC spin column (Millipore; Bedford, Mass.). PCR products are cloned into the pGEM™-T Easy vector system (Promega; Madison, Wis.).

To make the DHFR plasmid construct, p807, the pET-15b vector (Novagen, Madison, Wis.), is digested with Nde I and Bam HI, then treated with calf intestinal alkaline phosphatase (Promega; Madison, Wis.). The PCR subclone of the *M. avium* fol A gene in pGEM®-T Easy vector is digested with Nde I and Bam HI, then the restriction enzyme digested-fragments of the *M. avium* DHFR gene are isolated in a 0.8% agarose gel and the DNA eluted from the gel slice. The DNA is directionally cloned into the pET- 15b expression system using the Ligation Express™ kit (Clontech; Palo Alto, Calif.) with the start codon in close proxniity to the T7 promotor.

Example 5

Expression of Recombinant *M. Avium* DHFR

The host strain BL21(DE3)plysS, containing the DHFR recombinant gene in p807, is grown in LB broth (J. Sambrook et al., *Molecular Cloning: a Laboratory Manual* (second ed.), 1989) with 100 μg/ml ampicillin at 28° C. to an $A_{600}$ of 1.0 and expression induced with 0.1 mM IPTG overnight. The complementation plasmid p502, in the deficient strain D3-157 is grown under the same conditions in LB broth with 50 μg/ml thymidine; 100 μg/ml ampicillin and 100 μg/ml streptomycin. Thirty ml samples of cultures are washed twice with cold standard DHFR assay buffer and the pelleted cells are stored overnight at −20° C. Cells are resuspended in one ml of cold assay buffer and lysed by sonication. The insoluble proteins are pelleted at 16,000 g in a microcentrifuge at 4° C. and the supernatant assayed for DHFR activity, as described below.

Example 6

Purification and Thrombin Cleavage of Recombinant DHFR

Recombinant *M. avium* DHFR may be expressed and purified under denaturing conditions using His•Bind resin (Novagen; Madison, Wis.), taking advantage of the His•Tag fusion protein. The *M. avium* DHFR gene in p807 was expressed in BL21(DE3)plysS as described above, except that it was grown at 37° C. and induced with 1 mM IPTG for three hours. Cells were washed once with ice cold PBS and stored at −20° C. Recombinant fusion protein was purified from the inclusion bodies following the protocol in the pET System Manual, 4th Ed. (1994), and eluted from the His•Bind resin column with 300 mM imidazole. His•Tag fusion protein was then cleaved from 140 μg of recombinant protein with 0.82 Units of Thrombin (Novagen; Madison, Wis.) in 100 μg of 1×Thrombin cleavage buffer (20 mM Tris, pH 8.4; 0.15 M NaCl; 2.5 mM $CaCl_2$) at RT overnight. SDS PAGE analysis was performed with a 4–20% polyacrylamide gel (ICN Pharmaceuticals, Inc.; Costa Mesa, Calif.) with Perfect Protein™ molecular weight markers (Novagen; Madison, Wis.) and stained with Colloidal Coomassie Solution (ICN Pharmaceuticals, Inc.; Costa Mesa, Calif.) according to the manufacturer's protocol.

Figure 8:
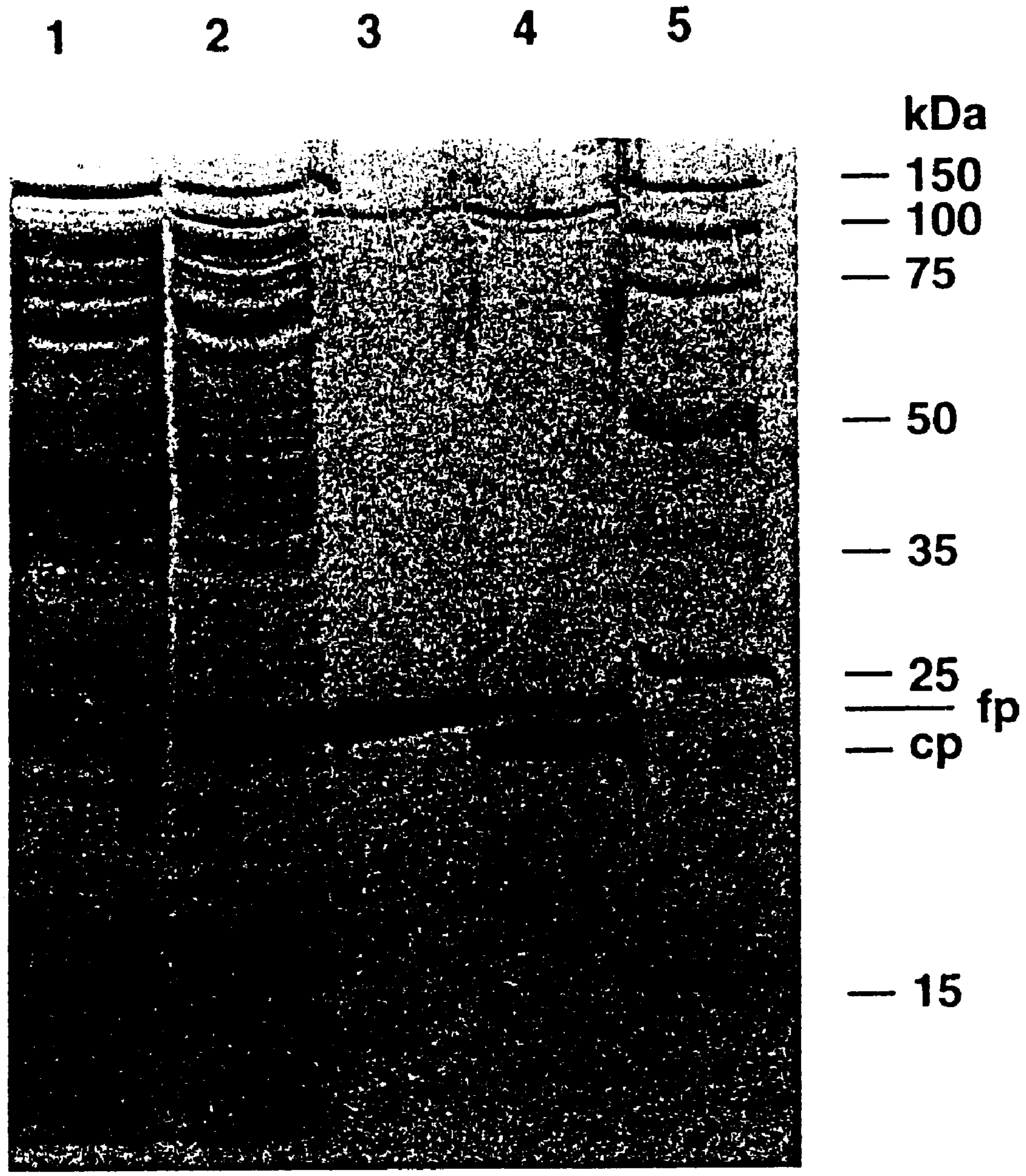
FIG. 8 SDS PAGE of *M. avium* DHFR expressed from BL 21 (DE3) plyS/p807.

Recombinant protein was expressed as a 22 kDa band that was not present before induction with IPTG. FIG. 8 depicts SDS PAGE analysis of the expression of *M. avium* DHFR in BL21(DE3)plysS/p807. Proteins were analyzed by SDS PAGE, noninduced culture (40 μg) (Lane 1), culture induced with 1 mM IPTG (40 μg) (Lane 2), *M. avium* DHFR His•Tag fusion protein purified on His•Bind resin (7 μg) (Lane 3), and Thrombin cleaved (indicated as "cp" for cleaved protein) and uncleaved *M. avium* DHFR (10 μg) (indicated as "fp" for fusion protein) (Lane 4). Molecular weight markers are indicated in kilodaltons (kDa) (Lane 5). As indicated in FIG. 8, when the recombinant protein was purified on a His•Bind resin column and cleaved with thrombin to remove the His•Tag fusion protein, a 20 kDa band of cleaved protein could be seen which is in close agreement with the predicted size of the protein (19.9 kDa), based upon the polypeptide sequence (FIG. 8).

Example 7

Activity of Recombinant DHFR

Both recombinant *M. avium* DHFR plasmid constructs (p807 and p502) were expressed under slow growth conditions at 28° C. to maximize the amount of DHFR expressed as soluble protein. Enzyme assays were performed on crude cell lysates from the plasmid constructs expressed in both the deficient strain D3-157 and the expression strain BL21 (DE3)plysS. As indicated in Table 2, DHFR activity was present in the deficient strain *E. coli* D3-157, containing the p502 complementation plasmid, but as expected, not in the D3-157 strain containing only pBS+ without the *M. avium* DHFR gene insert. Also, in the DHFR-proficient host strain BL21(DE3)plysS, DHFR specific activity was 1000-fold greater in the presence of the recombinant DHFR plasmid p807 than with the plasmid pET-15b without the recombinant DHFR gene.

TABLE 2

Expression of the DHFR Recombinant Gene and Enzyme Activity in *Escherichia coli*†

| Plasmid | *E. coli* Host Strain | Protein (mg/ml) | DHFR $10^{3}$ Units/ml | Specific Activity $10^3$ Units/mg |
|---|---|---|---|---|
| p502 | D3-157 | 34.1 ± 3.1 | 290 ± 5.8 | 8.5 ± 0.95 |
| pBS+ | D3-157 | 37.8 ± 2.6 | <1.6 | <0.042 |

TABLE 2-continued

Expression of the DHFR Recombinant Gene and Enzyme Activity in *Escherichia coli*†

| Plasmid | *E. coli* Host Strain | Protein (mg/ml) | DHFR $10^3$ Units/ml | Specific Activity $10^3$ Units/mg |
|---|---|---|---|---|
| p807 | BL21(DE3)plys S | 21.7 | 25,000 | 1,200 |
| pET-15b | BL21(DE3)plys S | 13.5 | 16 | 12 |

†Data with p502 and pBS⁺are presented as the mean and standard deviation of three samples. Values listed for pET-15b are from one sample and those for p807 are the mean of two samples.

Example 8

Dihydrofolate Reductase Assay

Dihydrofolic acid($FAH_2$), NADPH(tetrasodium salt), 2-mercaptoethanol and EDTA were obtained from Sigma (St. Louis, Mo.). $FAH_2$(20 mM) was suspended in 5 mM HCl containing 50 mM 2-mercaptoethanol and stored at −20° C. until used for assay. On the day of assay, the $FAH_2$ suspension was dissolved in 50 mM potassium phosphate buffer (pH 7) and kept on ice.

DHFR activity was measured at 30° C. in a Spectronic Genesis 5 Spectrophotometer as the decrease in the $A_{340}$. The reaction mixture was modified from that described by Al-Rubeai and Dale (M. Al-Rubeai, Biochem. 235:301–303, 1986) for the assay of DHFR from *Mycobacterium phlei* and consisted of 10 mM 2-mercaptoethanol, 0.1 mM NADPH, 0.1 mM $FAH_2$ and 0.01–0.05 ml of enzyme in a standard buffer of 50 mM potassium phosphate-1 mM EDTA, pH 7. The total assay volume was one ml. The reaction was initiated by the addition of $FAH_2$ after preincubation of the other components for 3 min. Dihydrofolate reductase activity was corrected for NADPH oxidase activity which was measured as a decrease in $A_{340}$, in the absence of $FAH_2$ during the preincubation period. One unit of enzyme is defined as the amount which reduces 1 μmole of $FAH_2$ per min using a molar extinction coefficient at $A_{340}$ of 12,300 $M^{-1}$ $cm^{-1}$ (B. L. Hillcoat et al., Anal. Biochem. 21:178–89, 1967).

Example 9

Use of PCR for Cloning From Genomic DNA

Figure 3:
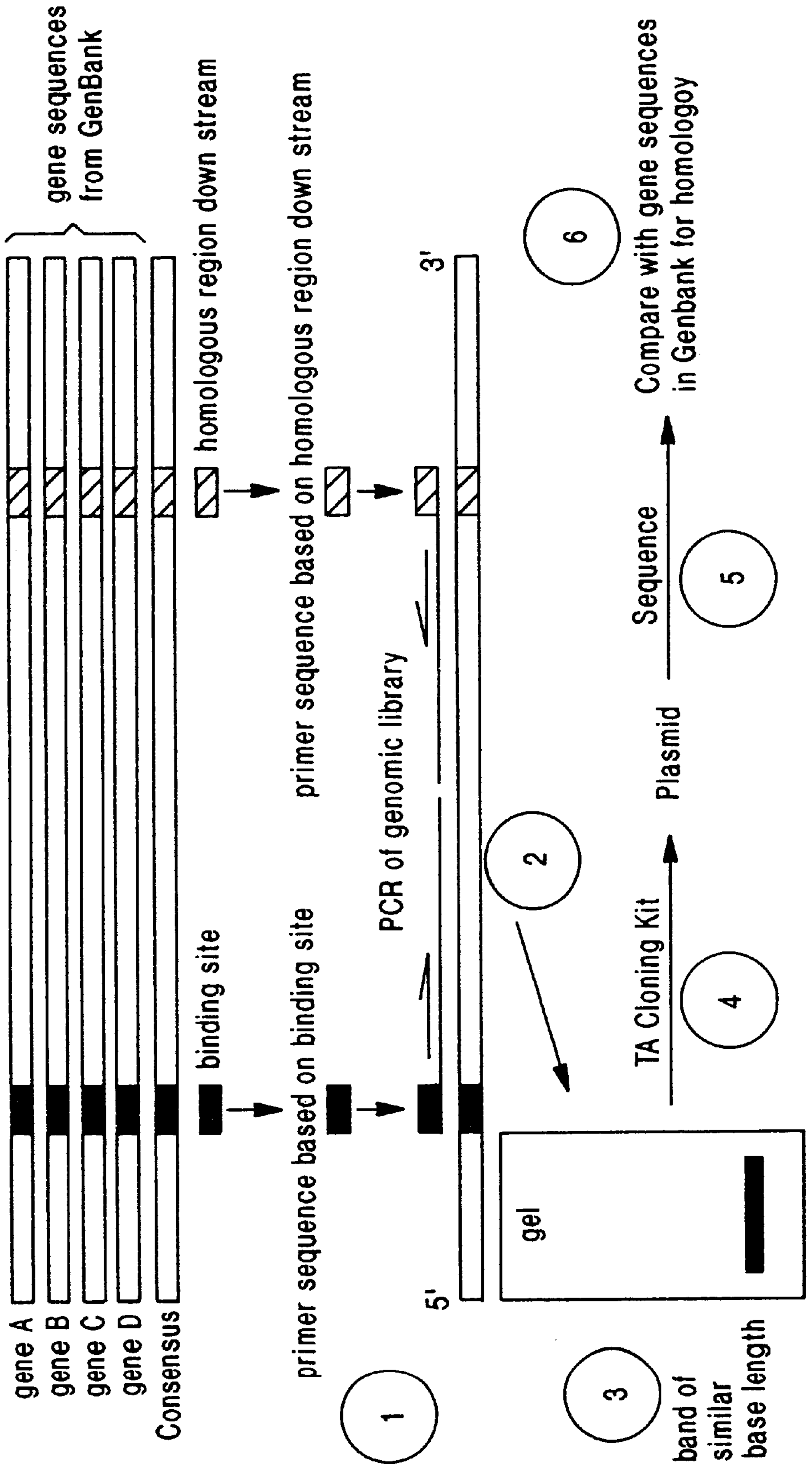
FIG. 3 Flow diagram depicting PCR procedure to search for the DHFR gene in *M. avium.*

FIG. 3 is a flow diagram outlining a general procedure to search for the DHFR gene in *M. avium* using PCR to clone the DHFR gene from genomic DNA. This may be accomplished by the following steps:

1. Sequences of DHFR genes from related species in question may be obtained from the GenBank and aligned by means of computer programs to yield areas of consensus. For instance, analysis of nucleotide and predicted amino acid sequences may be performed using Genetics Computer Group Sequence Analysis Software for the VAX (GCG; Madison, Wis.). Predicted peptide sequences may be translated with the PEPDATA program, nucleotide and peptide sequence alignments may be carried out using GAP, PILEUP and PRETTYBOX programs in the GCG package. The known DHFR genes, *S. aureus, S. epidermidis, B. subtilis*, and *L. casei* are the most closely related to Mycobacterium areas of homology, particularly those known from the literature to be involved in binding of trimethoprim, methotrexate, and the cofactor NADPH. These may be used to make primers for PCR. The choice for an ambiguous nucleotide that may occur within the consensus region may be made based on the known codon preference of *M. tuberculosis*. Primers may be 20–30 bases in length and may be synthesized commercially (Genosys).
2. Primers may be used in a PCR reaction to amplify respective areas from genomic DNA.
3. PCR products may be separated on a gel and examined for bands corresponding to segments containing the number of bases expected in the gene product.
4. A commercial Cloning Kit may be used to clone the PCR product into a plasmid.
5. Products may then be sequenced.
6. The sequences of the products may be compared with gene sequences in the GenBank to determine degree of homology.

Example 10

Bacteriophage Genomnic Library Screening

FIG. 4 is a flow diagram of procedures which may be used for screening genoric libraries for the DHFR gene in species such as *M. avium*. As indicated in FIG. 4, the following steps may be used for Genomic library screening:

1. Genomic Library (phage stock) may be used to infect *E. coli* (e.g. XL-1 Blue mrf' for λZAPII; Stratagene).
2. Lysis of *E. coli* takes place.
3. Using nylon membrane, DNA blots are made of plaques.
4. A probe will be made using the aligned sequences. Regions of homology will be chosen for use as a probe and a 50 base pair oligo will be synthesized commercially. The probe is nonradioactively labeled with digoxigenin.
5. Membranes are processed, leaving single-stranded DNA fixed. Membranes are incubated with digoxigenin-labeled probe to identify the original sites of plaques carrying the transformed gene. Positive sites are detected by fluorescent tag, using the Genius™ system (Boehringer Mannheim).
6. Insert is sequenced and compared with gene sequences in GenBank for homology.
7. Alternatively, a sublibrary may be screened with a DNA probe: Genomic DNA is digested with a restriction enzyme, run on an agarose gel, transferred to a nylon membrane and hybridized with a probe made to a homologous region in a Southern blot hybridization. The DNA in the region of the gel that hybridizes to the probe is eluted from the gel and used to make a plasmid library that will potentially contain the gene. This sublibrary can be plated in *E. coli* and screened with the same Southern blot conditions as with the genomic blot to identify the clones containing the homologous sequence. These clones may then be sequenced and compared to the sequences from the GenBank.

Example 11

Genetic Complementation Cloning

FIG. 5 is a flow diagram depicting a procedure which may be used for genetic complementation cloning, and gene cloning by deduced amino acid sequences. Genetic complementation cloning can be performed by the following steps:

1. Excision of lambda ZAP genomic library from phage to plasmid form.
2. Complementation of deficient strain of *E. coli.*
3. Growth of gene complemented mutant on minimal medium containing appropriate substrate.
4. Pick colonies, culture, and isolate plasmids. Perform restriction enzyme digestion and Southern Blot. Probe blot with oligonucleotide with sequence analogous to binding site.
5. Subclone DNA fragments that hybridize with probe and sequence.

Example 12

Genetic Cloning by Deduced Amino Acid Sequence

Gene cloning by deduced amino acid sequence as depicted in FIG. 5 may be accomplished by the following steps:

1. The native DHFR protein from *M. avium* is purified, isolated on an SDS PAGE gel and transferred to polyvinylidene difluoride membrane. The protein is excised from the membrane and subjected to N-terminal sequencing.
2. The nucleotide sequence of the peptide can then be deduced and the sense strand used as one of the primers for PCR.
3. Internal peptides may be obtained by cleavage of the native DHFR protein into smaller peptides that may be purified and sequenced as above. The antisense nucleotide sequence from these peptides may be used as the opposing primer in a PCR reaction with genolnic *M. avium* DNA.
4. The PCR product from this reaction may be cloned into *E. coil* and sequenced. This partial sequence of the DHFR gene may then be used to probe the Genomic library to obtain a clone containing the entire DHFR gene sequence.

Example 13

Expression and Purification of Recombinant DHFR

The Mycobacterium DHFR gene may be cloned into the pTrcHis System (Invitrogen; San Diego, Calif.) for expression in *E. coli*. Restriction enzyme sites can be added to the 5' and 3' ends of the cDNA respectively by polymerase chain reaction (PCR) using primers containing these sites. PCR can be performed with Taq DNA polymerase (Perkin-Elmer Cetus; Norwalk, Colo.) under conditions recommended by the manufacturer. The PCR product can be cloned into the pTrcHis vector in close proximity to the *E. coli* promotor and expressed in TOPIO™ cells (Invitrogen; San Diego, Calif.) according to the manufacturer's protocol. *E. coli* containing recombinant plasmid can be grown in the presence of 0.1 mg ampicillin/ml and expression can be induced by the addition of 1 mM IPTG. The cell pellet can be disrupted in a French Press (3× at 15,000 lb/inch$^2$) in ice cold lysis buffer and the recombinant protein purified by using a His/tag fusion protein with the Invitrogen affinity purification system. This procedure was used successfully to express the putative (and incorrect) DHFR gene listed in GenBank as Accession No. X59271.

Example 14

Use of *M. avium* DHFR Sequence to Identify Other Sequences

The disclosed *M. avium* DHFR sequence may be used to identify corresponding DHFR genes in mycobacteria other than *M. avium* as well as in other species. The *M. avium* DHFR nucleic acid sequence, or portions thereof, may be used to make probes and PCR primers. These probes and primers may then be used to identify regions of homology on other genes. Regions particularly useful to identify corresponding DHFR genes include sequences encoding the portions of the DHFR protein involved in the binding of trimethoprim, methotrexate and NADPH.

For example, target DHFR sequences may be screened with a probe incorporating all or part of the mycobacterial DHFR nucleic acid sequence. Oligo probes may be made from the binding sites of trimethoprim, methotrexate and NADPH on the DHFR gene, and used in a Southern Blot reaction with genomic DNA from the target sequence. The probe hybridizes to genomic DNA of the target having homologous regions. To facilitate this process, target sequences may be hybridized with $^{32}$P-radiolabeled oligo probes homologous to binding site regions on the *M. avium* DHFR gene. Specific procedures involving the use of probes to identify homologous regions on target sequences are outlined in FIG. 4. The nucleic acid sequence of the invention can be substituted and used in probes in these same procedures, to identify corresponding DHFR genes in species other than *M. avium.*

Example 15

Cell-free Enzyme System and Purification of DHFR From Mycobacteria

A crude cell-free DHFR enzyme system may be prepared directly from mycobacteria. Procedures for cell disruption and isolation of subcellular fractions may include probe sonication for disruption of mycobacteria. Alternatively, the Bead Beater (commercially available), which results in far better breakage of mycobacteria, may be used. The Bead Beater is used to obtain crude enzyme preparations. Before use, the Bead Beater is washed, rinsed with ethanol, and allowed to dry. The chamber is filled with sterilized glass beads and the breaking buffer added to wet beads. Breaking buffer consists of a 10 mM Tris-HCl solution (pH 7.4) with 150 mM NaCl, 10 mM EDTA, and 0.1% Tween 80. Following sterilization by autoclaving, the following are added before filter sterilzation (per 100 ml of buffer): 1) DNase and RNase, 0.06%, 2) 23.3, μl of a3 mg/ml stock of Pepstatin in ethanol(−20° C.) 3) 50 μl of a 1 mg/ml stock of Leupeptin in ethanol (−20° C.) 4) 200 μl of a 100 mM stock of PMSF in isopropanol (−20° C.). mycobacteria are added to chamber in the breaking buffer solution and pulsed for 30 seconds (x's 8) with cooling. 20–24 g of wet weight (from 6 liters of mycobacteria) was used in 25-ml of buffer. Following breakage, the amount of protein is quantitated by the Bradford procedure (M. M. Bradford, Anal. Biochem. 72:248–254, 1976) to determine optimnum breakage (N. Ramasesh et al., Infect. Immun. 60:308–311, 1992). Disrupted cell suspension is transferred to 50-ml conical centrifuge tubes and centrifuged at 4,000×g to pellet unbroken cells and glass beads. Supematant is centrifuged at 40,000×g for 2 hr to obtain a crude supernatant. This is filtered through a 0.45 μm filter (low-protein binding), followed by a 0.2 μpm filter (low-protein binding) to remove any unbroken mycobacteria. Proteins are precipitated from the resulting supernatant by slow addition of ammonium sulfate, on ice with stirng, to 80% saturation. The resulting suspension is then stored at −20° C. until used in assays. Prior to DHFR assay, a measured volume of the crude enzyme preparation is centrifuged at 2–8° C., the supernatant is discarded, and the pellet is dissolved in an equal volume of cold 50 mM potassium phosphate containing 1 mM EDTA, pH 7.

Example 16

Isolation and Purification of DHFR

The crude cell-free enzyme preparation of Example 15 (80% ammonium sulfate precipitate) can be centriftged at 0–4° C., the supernatant discarded, and the pellet dissolved in cold standard buffer. The proteins can then be fractionated at 0–4° C. using solid ammonium sulfate at successive saturations of 25, 40, 50, 60 and 80%. Enzyme activity can be measured in each fraction, after dissolution in standard buffer, and the active fractions pooled. The protein concentration of pooled fractions can be measured to determine specific activity (units/mg of protein). Further purification can be accomplished by gel filtration chromatography (A. M. Albrecht et al., Biochem. 8:960–967, 1969; A. M. Albrecht et al., Ag. Biochem. Biophys. 153:16–25, 1972), followed by methotrexate affinity chromatography (B. T. Kaufinan, Meth. Enzymol. 34:272–81, 1974; T. D. Meek et al., Biochemist. 24:678–686, 1985; W. Sirawarapom et al., Exper. Prasitol. 72: 184–90, 1991). A 4% beaded agarose matrix is available from Sigma. Gel filtration chromatography can be done on a Sephadex G-75 column equilibrated with standard buffer. Fractions can be monitored for protein by measuring their absorbance at 280 nm and for DHFR activity. Active fractions can be pooled and total and specific enzyme activity determined. Gel filtration has been used successfully for the partial purification of *M. phlei* DHFR (M. Al-Rubeai et al., Biochem. J. 235:301–3, 1986). However, it may be necessary to add bovine serum albumin (1 mg/ml) to stabilize the enzyme. This step is initially performed on a small scale to determine the stability of the enzyme before proceeding further with the purification. Purified DHFR can be characferized by SDS PAGE to determine molecular weight.

Once purified enzyme preparations are obtained, the apparent $K_m$ for dihydrofolate and NADPH may be determined at saturating concentrations of each substrate and the $V_{max}$ may be determined using double reciprocal Lineweaver-Burk plots (I. H. Segal, *Biochemical Calculations*, 366–96, 1968). Double reciprocal plots with and without inhibitor can also be used to establish the nature of the inhibition (competitive or noncompetitive). The inhibition constant ($K_i$) of an inhibitor can be determined using Dixon plots of the reciprocal of the velocity vs. inhibitor concentration for increasing concentrations of DHFR.

Example 17

In Vitro Testing of Drugs Using a Wild-type or Recombinant Enzyme System

Table 3 presents the results of an experiment designed to establish that the substrate requirements for enzyme activity are those expected for DHFR and also that a linear relationship exists between rate of reaction and amount of enzyme. The upper portion of Table 3 presents results which demonstrate the requirement for both NADPH and dihydrofolate for enzyme activity, measured as the decrease in $A_{340nm}$ over time (30° C.). In the absence of either substrate, the change in absorbance at 340 nm/min is 10 to 20-fold less than when both substrates are present. The lower portion of the table demonstrates a linear relationship between reaction rate and enzyme amount. The conclusion from these results is that the assay is selectively measuring DHFR activity in the crude cell-free extract. The small amount of change in absorbance in the presence of either NADPH or dihydrofolate alone was due to oxidase activity or instability of dihydrofolate, respectively.

TABLE 3

Requirements of *M. avium* DHFR for NADPH and Dihydrofolate ($FAH_2$) and Relationship of Rate to Enzyme Amount

| μl Enzyme Preparation | NADPH | $FAH_2$ | Δ A340 nm/min. |
|---|---|---|---|
| 50 | + | − | −0.0070 |
| 50 | + | + | −0.0740 |
| 50 | − | + | −0.0041 |
| 50 | + | + | −0.0930 |
| 15 | + | + | −0.0230 |
| 30 | + | + | −0.0440 |
| 30 | + | + | −0.0470 |
| 60 | + | + | −0.0950 |

Because of the demonstrated linear reaction rate with endogenous or wild type DHFR, recombinant enzyme of the present invention should demonstrate the same activity and thus may be used to screen and identify drugs and other agents with activity against DHFR. In one experiment to screen for potential antimycobacterial agents, the drugs may be dissolved in DMSO followed by 10-fold serial dilutions in a final concentration of 10% DMSO. Ten μl of each drug dilution will be added to the reaction miuxture having a total volume of 1 ml. Both enzyme and drug will be preincubated together for 3 minutes before the reaction is started by the addition of dihydirofolate. The reaction rate will be monitored both before and after dihydrofolate addition and the change in absorbance corrected for endogenous NADPH oxidase activity. The reaction rate, percent inhibition and approximate $IC_{50}$ will be calculated to deterimne the effect, if any, of the agent on the DHFR.

The enzyme reaction rate may be calculated as follows:

Δ A340 nm/minute corrected for oxidase activity (mean±0.0019, n=11)

The % inhibition may be calculated as follows:

$$\frac{\Delta A340\ \mathrm{nm}(0.1\%\ DMSO) - \Delta A340\ \mathrm{nm}(inhibitor)}{\Delta A340\ \mathrm{nm}(0.1\%\ DMSO)} \times 100$$

The $IC_{50}$ may be calculated as follows:

The amount of inhibitor required to inhibit the reaction rate by 50%.

Example 18

Deterrninmg Inhibitory Activity of DHFR Inhibitors in Various Systems

As noted in Example 17, potential DHFR inhibitors can be tested in cell-free enzyme systems containing wild-type DHFR and/or enzyme systems containing the recombinant enzyme of the present invention. This is useful to obtain data for CoMFA, discussed below. In one cell-free enzyme system, DHFR activity may be measured at 30° C. as the decrease in absorbance at 340 nm. The reaction mixture is adapted from that described by Al-Rubeai and Dale (M. Al-Rubeai et al., Biochem. J. 235:301–3, 1986) for DHFR from *Mycobacterium phlei* and consists of 10 mM 2-mercaptoethanol, 0.1 mM NADPH, 0.1 mM dihydrofolate and 0.01–0.05 ml of enzyme in a standard buffer of 50 mM potassium phosphate—1 mM EDTA, pH 7. The total assay volume is 1 ml. Dihydrofolate is added to initiate the reaction after the other components are preincubated for 3 minutes. Activity is corrected for NADPH oxidase activity that is measured in the absence of dihydrofolate during the preincubation period. For inhibition assays, the inhibitor and enzyme are added before the 3 minute preincubation period. One unit of enzyme is defined as that amount that reduces 1 μmole of DHFR per minute using a molar extinction coefficient at 340 nm, of 12,300 $M^{-1}$ $^{cm-1}$ (B. L. Hillcoat et al., Anal. Biochem. 21:178–89, 1967). The $IC_{50}$ can be determined as the amount of inhibitor required to inhibit the reaction rate by 50% under a defined set of conditions.

In addition to cell-free systems, intracellular activity of candidate compounds may also be evaluated. Two established cell lines available for determining intracellular activity of antimycobacterial drugs are the murine J774 macrophage cell line and the human Mono Mac 6 monocytic cell line (E. L. Wright et al., J. Clin. Microbiol. 34, 1996). Both cell lines can be infected with *M. tuberculosis* (E. L. Wright et al., J. Clin. Microbiol. 34, 1996) and *M. avium*. Essentially three concentrations of drug can be tested, the MIC value (predetermined in TAACF or broth microdilution assay at SRI), a concentration 3-fold above the MIC and a concentration 3-fold below the MIC concentration.

The testing procedure may consist of two stages. In the first stage, the toxicity of each drug may be tested using a MTT Cytotoxicity Assay Kit (Advanced Tissue Sciences) (E. L. Wright et al., J. Clin. Microbiol. 34, 1996). This can be done with both cell lines. The percent of untreated control for each dilution of a given test compound is plotted on the y-axis vs. the concentration of the test compound on the x-axis. $LD_{50}$ (i.e. $IC_{50}$) endpoints are then determined from the graph by reading from where the 50% point intercepts the Dose Response Curve to the concentration along the x-axis. That concentration is the $LD_{50}$ value. Drugs that are cytotoxic at relevant concentrations will not be tested further, but information gained from this is useful in developing more selective and less toxic derivatives.

In a second stage of testing, macrophage cell lines may be used to examine the effectiveness of each drug to inhibit intracellular growth of *M. tuberculosis* and *M. avium* (*M. tuberculosis* H37Ra or H37Rv and *M. avium* serovar 4) and several *M. avium* and *M. tuberculosis* strains. Briefly, the J774 cell line is maintained in RPMI, containing 10% fetal bovine serum (FBS). At the time of infection with mycobacteria, the FBS is decreased to 1% to reduce division of J774 cells (N. Rastogi, Curr. Microb. 16:79–92, 1987). J774 cells are infected with mycobacteria for four hours, after which time cells are washed and fresh media added with appropriate concentrations of drugs. Cells are exposed to 3 different concentrations of each drug to be tested with the drugs being replenished daily, by topping off. The infection is allowed to continue for 5 days. J774 cells are lysed with sodium dodecyl sulfate at time zero (immediately after infection), and at five days to release the mycobacteria. Viable mycobacteria are enumerated by plating on 7h10agar. In parallel with in vitro combination drug studies, lipophilic DHFR inhibitors may be evaluated in the macrophage cell lines for synergy in combination with the following drugs: isoniazid, ethambutol, and rifampin. Evaluation of the in vitro drug combination studies may be helpful before this phase is initiated and other antimycobacterial agents can be added to this scheme or replace one of the three listed here.

The Mono Mac 6 cell line may be obtained from the German Collection of Microorganisms and Cell Cultures, Braunschweig, Germany. This cell line is a human acute monocytic leukemia. Cells are grown as a suspension culture and are maintained in RPMI 1640, containing 10% (v/v) FCS, 2 mM L-glutamine, nonessential anino acids, 1 mM Na-pyruvic acid, and 9 μg/ml of bovine insulin (Sigma Chem. Co.; St. Louis, Mo.). The Mono Mac 6 cell line is the only human cell line to constitutively express phenotypic and functional features of mature monocytes (H. W. L. Ziegler-Heitbrock et al., Int. J. Cancer. 41:456–61, 1988). Unlike the U937 and THP-1 human monocytic cell lines that must be induced to develop phagocytic properties (F. Herrmann, J. Exp. Med. 162:1111–16, 1985), the MM6 cell line can constitutively phagocytize antibody-coated erythrocytes (H. W. L. Ziegler-Heitbrock et al., Int. J. Cancer. 41:456–61, 1988) and mycobacteria (J. S. Friedland et al., Cytokine 5:150–56, 1993; R. J. Shattock et al., J. Gen. Virology 75:849–56, 1994). For experiments involving drug inhibition studies, the J774 cell line may be infected with five mycobacteria per macrophage for four hours. For the Mono Mac 6, ten mycobacteria per macrophage are required, and overnight infection is necessary. The rest of the method is the same.

Activity of select compounds may also be evaluated in a mouse model. *M. tuberculosis* H37Rv infected mouse model may be used for single and combination drug evaluation involving 1–3 drugs, tested individually, and in combination with rifampin and in combination with isoniazid and in the *M. avium* infected Beige model.

In addition to the foregoing, other models known in the art for evaluating inhibition of DHFR of various species, such as mammalian systems, may be used, and the data from these experiments correlated with data obtained using the recombinant enzyme of the present invention.

Example 19

Use of CoMFA Analysis

3-D QSAR CoMFA analysis may be used to determine if there is any correlation between an agent's structure and its ability to inhibit DHFR. The $IC_{50}$ values of existing compounds or newly synthesized analogs can be determined against isolated mycobacterial DHFR enzyme. The CoMFA analysis should encompass the areas critical to enzyme binding in order to obtain the most information from the analysis.

A CoNFA analysis of target drugs using inhibitory data from mammalian systems may also be done. Comparison of a mammalian binding model with the analysis derived from the mycobacterial enzyme inhibition data should increase the ability to predict alterations in structure that can not only enhance binding to the mycobacterial DHFR, but should also increase selectivity versus the mammalian enzyme. CoMFA analysis may also be done on the *M. avium* DHFR enzyme itself.

Actual CoMFA can be performed using the TRIPOS software (SYBYL 6.2 version). The analysis consists of the following: 1) establishing the conformation of each molecule; 2) superimposing each of the conformations from step 1; 3) calculating for each of the interaction energies with suitable probes at many points on a lattice; 4) performing a statistical analysis of the relationship between the interaction energies and the property of interest ($IC_{50}$ for DHFR inhibition); and 5) displaying the 3-D QSAR coefficient contour map. The final contour map gives a real sense in space where the QSAR terms have high or low values and can be obtained for both the steric and electrostatic terms. A contour map represents in real space a picture of what portions of the molecule positively and negatively affect the biological property of interest either electrostatically or sterically. From these maps, one can predict what modifications can enhance biological activity. In fact, further computer analysis using the model for second generation targets can predict biological activity of these new targets. One method of predicting new structures for synthesis and screening is based on the SYBYL program LEAPFROG. One can obtain a hypothetical binding cavity based on the CoMFA. This program can be used to predict new structures using molecular probes and binding energies to the cavity can be calculated for these structures.

Once the CoMFA is performed on a suitable number of agents, a rational approach based upon the inhibition data, the CoMFA results, and previous experience with antifolate drug design may be used to produce more selective second generation DHFR inhibitors. Computer modeling programs such as LEAPFROG can be used for second generation compounds and to test the validity of the CoMFA model by comparing predicted $IC_{50}$ values with those obtained experimentally. As more compounds with data are generated, the CoMFA model can be updated to increase its predictive power and the quality of the hypothetical binding cavity. This work dovetails into and complements additional experiments once the crystal structures of inhibitors in the mycobacterial DHFR active site are actually obtained. Structures of compounds in the active site can be compared to the minimized structures derived from CoMFA model and the actual enzyme active site can be grossly compared to the putative DHFR cavity generated by LEAPFROG.

Other embodiments and uses of the invention will be apparent to those skilled in the art from consideration of the specification and practice of the invention disclosed herein. All docunents, including U.S. patents and applications disclosed herein, are specifically incorporated herein by reference. U.S. provisional patent application serial No. 60/034,725, filed Jan. 3, 1997, and U.S. provisional patent application serial No. 60/039,737, filed Feb. 14, 1997, both of which are entitled *Mycobacterium avium* fol A gene that encodes for the enzyme, Dihydrofolate Reductase (DHFR), are both specifically incorporated by reference. The specification and examples should be considered exemplary only with the true scope and spirit of the invention indicated by the following claims.

We claim:

1. A method for screening for an agent that inhibits the activity of a DHFR protein of a Mycobacterium comprising the steps of:

a. determining the activity of a recombinant DHFR protein upon incubation with each of a plurality of agents wherein said recombinant DHFR protein contains the sequence of SEQ ID NO 2 or an active portion thereof as compared to activity in the absence of said each agent; and b. selecting the agent that inhibits recombinant DHFR protein activity.

2. The method of claim 1 wherein the Mycobacterium is *M. avium, M. bovis, M. tuberculosis* or *M. leprae.*

3. The method of claim 1 wherein the active portion is an enzymatically active portion.

4. The method of claim 1 wherein the active portion is an antigenically active portion.

5. The method of claim 1 wherein the plurality comprises greater than $10^2$ different agents.

6. The method of claim 1 wherein the plurality of agents comprises a collection of related chemical compounds.

7. The method of claim 6 wherein the collection comprises chemical modifications of folate, methotrexate, trimethoprim, quinazoline or combinations thereof.

8. The method of claim 1 wherein incubating comprises mixing the recombinant DHFR protein with the agent under conditions that allow for a molecular interaction.

9. The method of claim 8 wherein the molecular interaction is binding.

10. The method of claim 1 wherein the activity inhibited is enzymatic activity.

11. The method of claim 1 wherein the activity inhibited is immunogenicity.

12. The method of claim 1 further comprising the step of determining the molecular conformation of said agent.

13. The method of claim 1 further comprising the steps of selecting a plurality of agents that inhibit the activity of the Mycobacterium DHFR protein, determining the molecular conformation of each agent selected and identifying a common inhibitory molecular conformation.

14. A method for assessing the ability of an agent to inhibit the activity of a Mycobacterium DHFR protein comprising:

a. incubating a recombinant mycobacterial DHFR protein with said agent wherein said recombinant mycobacterial DHFR protein contains the sequence of SEQ ID NO 2 or an active portion thereof;

b. determining the activity of the incubated recombinant mycobacterial DHFR protein; and c. comparing the activity determined with activity in the absence of said agent.

15. The method of claim 14 wherein the activity is enzymatic activity.

16. The method of claim 14 wherein the activity is immunogenicity.

17. The method of claim 14 wherein the step of incubating comprises mixing the agent with the recombinant mycobacterial DHFR protein under physiological conditions.

18. The method of claim 17 wherein the agent selected is usefuil for the treatment of a mycobacterial infection.

19. The method of claim 14 wherein the Mycobacterium DHFR protein is of a specific species selected from the group consisting of *M. avium, M. bovis, M. tuberculosis*, and *M. leprae*, and the agent is specific for the treatment of the same species.

20. A method for selecting an antimycobacterial agent comprising:

a. analyzing a molecular conformation of a recombinant mycobacterial DHFR protein wherein said recombinant mycobacterial DHFR protein contains the sequence of SEQ ID NO 2 or an active portion thereof;

b. identifying a binding site within the molecular conformation; and c. selecting the agent with a molecular structure that fits within the binding site and that has therapeutic activity against a Mycobacterial infection.

21. The method of claim 20 wherein the binding site is a substrate binding site.

22. The method of claim 20 wherein the molecular conformation is analyzed from crystallographic analysis.

23. The method of claim 20 wherein the molecular conformation is analyzed from structure-activity relationships of the recombinant mycobacterial DHFR protein with a plurality of DHFR protein substrates.

* * * * *

SEQUENCE LISTING

```
<160> NUMBER OF SEQ ID NOS: 14

<210> SEQ ID NO 1
<211> LENGTH: 660
<212> TYPE: DNA
<213> ORGANISM: Artificial Sequence
<220> FEATURE:
<221> NAME/KEY: CDS
<222> LOCATION: (57)..(599)
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 1
gacgtcgtgg tgcacaacta cgatccgcac ccggccatca aggcccccgt cgcggt atg      59
                                                              Met
                                                                1 acc cgt gcc gag gtg ggc ctg gtg tgg gcc cag tcg acg tct ggc gtc      107
Thr Arg Ala Glu Val Gly Leu Val Trp Ala Gln Ser Thr Ser Gly Val
            5                  10                  15 atc ggc cgc ggc ggt gac atc ccg tgg agc gtg ccc gag gac ctc acc      155
Ile Gly Arg Gly Gly Asp Ile Pro Trp Ser Val Pro Glu Asp Leu Thr
        20                  25                  30 cgg ttc aaa gag gtg acc atg ggg cac acc gtg atc atg ggc cgg cgg      203
Arg Phe Lys Glu Val Thr Met Gly His Thr Val Ile Met Gly Arg Arg
    35                  40                  45 acc tgg gag tcg ttg ccg gcc aag gtg cgg ccg ctg ccc ggc cgg cgc      251
Thr Trp Glu Ser Leu Pro Ala Lys Val Arg Pro Leu Pro Gly Arg Arg
 50                  55                  60                  65 aac gtg gtg gtg tcc cgc cgg ccc gac ttc gtc gcc gag ggg gcg cgg      299
Asn Val Val Val Ser Arg Arg Pro Asp Phe Val Ala Glu Gly Ala Arg
                70                  75                  80 gtg gcc ggg tcg ctg gag gcg gcc ctc gcg tac gcc ggg agc gac ccg      347
Val Ala Gly Ser Leu Glu Ala Ala Leu Ala Tyr Ala Gly Ser Asp Pro
            85                  90                  95 gcg ccg tgg gtg atc ggc ggc gcg cag atc tat ctg ctg gcg ctg ccc      395
```

-continued

```
Ala Pro Trp Val Ile Gly Gly Ala Gln Ile Tyr Leu Leu Ala Leu Pro
        100                 105                 110

cat gcc acc cgc tgc gag gtc acc gaa atc gag atc gac ctg cgc cgc      443
His Ala Thr Arg Cys Glu Val Thr Glu Ile Glu Ile Asp Leu Arg Arg
    115                 120                 125

gac gac gac gac gcg ctg gcg ccg gcg ctg gac gac agc tgg gta ggc      491
Asp Asp Asp Asp Ala Leu Ala Pro Ala Leu Asp Asp Ser Trp Val Gly
130                 135                 140                 145

gag acg ggc gag tgg ctg gcc agc cgc tcc ggg ctg cgg tac cgg ttc      539
Glu Thr Gly Glu Trp Leu Ala Ser Arg Ser Gly Leu Arg Tyr Arg Phe
                150                 155                 160

cac agc tac cgt cgg gac ccg cgc tct tcc gtt cgc ggc tgt tcg ccc      587
His Ser Tyr Arg Arg Asp Pro Arg Ser Ser Val Arg Gly Cys Ser Pro
            165                 170                 175

tca cgc ccg agc tgacatactc ggacgcgggg gtcggtcaca caccgtctac          639
Ser Arg Pro Ser
        180

cagccgctgt tcgggaaaag g                                              660


<210> SEQ ID NO 2
<211> LENGTH: 181
<212> TYPE: PRT
<213> ORGANISM: Artificial Sequence
<220> FEATURE:
<223> OTHER INFORMATION: Primer that can hybridise to flanking regions
      of pig microsatellites sequences

<400> SEQUENCE: 2

Met Thr Arg Ala Glu Val Gly Leu Val Trp Ala Gln Ser Thr Ser Gly
  1               5                  10                  15

Val Ile Gly Arg Gly Gly Asp Ile Pro Trp Ser Val Pro Glu Asp Leu
            20                  25                  30

Thr Arg Phe Lys Glu Val Thr Met Gly His Thr Val Ile Met Gly Arg
        35                  40                  45

Arg Thr Trp Glu Ser Leu Pro Ala Lys Val Arg Pro Leu Pro Gly Arg
     50                  55                  60

Arg Asn Val Val Val Ser Arg Arg Pro Asp Phe Val Ala Glu Gly Ala
 65                  70                  75                  80

Arg Val Ala Gly Ser Leu Glu Ala Ala Leu Ala Tyr Ala Gly Ser Asp
                85                  90                  95

Pro Ala Pro Trp Val Ile Gly Gly Ala Gln Ile Tyr Leu Leu Ala Leu
            100                 105                 110

Pro His Ala Thr Arg Cys Glu Val Thr Glu Ile Glu Ile Asp Leu Arg
        115                 120                 125

Arg Asp Asp Asp Asp Ala Leu Ala Pro Ala Leu Asp Asp Ser Trp Val
    130                 135                 140

Gly Glu Thr Gly Glu Trp Leu Ala Ser Arg Ser Gly Leu Arg Tyr Arg
145                 150                 155                 160

Phe His Ser Tyr Arg Arg Asp Pro Arg Ser Ser Val Arg Gly Cys Ser
                165                 170                 175

Pro Ser Arg Pro Ser
            180


<210> SEQ ID NO 3
<211> LENGTH: 79
<212> TYPE: PRT
<213> ORGANISM: Artificial Sequence
<220> FEATURE:
<223> OTHER INFORMATION: Primer that can hybridise to flanking regions
```

-continued

```
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 3

Met Ser Ile Ala Asp Arg Val Ile Gly Asn Pro Trp His Leu Pro Asp
  1               5                  10                  15

Leu Phe Lys Thr Gly Met Gly Arg Lys Thr Phe Glu Ser Ile Gly Arg
             20                  25                  30

Pro Leu Pro Arg Asn Ile Val Leu Thr Gln Pro Glu Gly Val Ser Leu
         35                  40                  45

Glu Gly Glu Ile Gly Gly Tyr Pro Ala Asp Leu Tyr Thr Ile Phe Gly
     50                  55                  60

Asp Thr Phe Pro Trp Val Ser Ser Glu Asp Glu Asn Phe Leu Arg
 65                  70                  75


<210> SEQ ID NO 4
<211> LENGTH: 19
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 4

Met Thr Arg Ala Glu Val Gly Leu Val Trp Ala Gln Ser Thr Ser Gly
  1               5                  10                  15

Val Ile Gly


<210> SEQ ID NO 5
<211> LENGTH: 161
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 5

Met Thr Leu Ser Ile Ile Val Ala His Asp Lys Gln Arg Val Ile Gly
  1               5                  10                  15

Tyr Gln Asn Gln Leu Pro Trp His Leu Pro Asn Asp Leu Lys His Val
             20                  25                  30

Lys Gln Leu Thr Thr Gly Asn Thr Leu Val Met Gly Arg Lys Thr Phe
         35                  40                  45

Asn Ser Ile Gly Lys Pro Leu Pro Asn Arg Arg Asn Val Val Leu Thr
     50                  55                  60

Asn Gln Ala Ser Phe His His Glu Gly Val Asp Val Ile Asn Ser Leu
 65                  70                  75                  80
```

-continued

```
Asp Glu Ile Lys Glu Leu Ser Gly His Val Phe Ile Phe Gly Gly Gln
                 85                  90                  95

Thr Leu Phe Glu Ala Met Ile Asp Gln Val Asp Asp Met Tyr Ile Thr
            100                 105                 110

Val Ile Asp Gly Lys Phe Gln Gly Asp Thr Phe Phe Pro Pro Tyr Thr
        115                 120                 125

Phe Glu Asn Trp Glu Val Glu Ser Ser Val Glu Gly Gln Leu Asp Glu
    130                 135                 140

Lys Asn Thr Ile Pro His Thr Phe Leu His Leu Val Arg Arg Lys Gly
145                 150                 155                 160

Lys


<210> SEQ ID NO 6
<211> LENGTH: 159
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 6

Met Ile Ser Leu Ile Ala Ala Leu Ala Val Asp Arg Val Ile Gly Met
  1               5                  10                  15

Glu Asn Ala Met Pro Trp Asn Leu Pro Ala Asp Leu Ala Trp Phe Lys
             20                  25                  30

Arg Asn Thr Leu Asn Lys Pro Val Ile Met Gly Arg His Thr Trp Glu
         35                  40                  45

Ser Ile Gly Arg Pro Leu Pro Gly Arg Lys Asn Ile Ile Leu Ser Ser
     50                  55                  60

Gln Pro Gly Thr Asp Asp Arg Val Thr Trp Val Lys Ser Val Asp Glu
 65                  70                  75                  80

Ala Ile Ala Ala Cys Gly Asp Val Pro Glu Ile Met Val Ile Gly Gly
                 85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155


<210> SEQ ID NO 7
<211> LENGTH: 159
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
```

-continued

<400> SEQUENCE: 7

Met Ile Ser Leu Ile Ala Ala Leu Ala Val Asp Arg Val Ile Gly Met
1 5 10 15

Glu Asn Ala Met Pro Trp Asn Leu Pro Ala Asp Leu Ala Trp Phe Lys
20 25 30

Arg Asn Thr Leu Asn Lys Pro Val Val Met Gly Arg His Thr Trp Glu
35 40 45

Ser Ile Gly Arg Pro Leu Pro Gly Arg Lys Asn Ile Val Ile Ser Ser
50 55 60

Lys Pro Gly Thr Asp Asp Arg Val Gln Trp Val Lys Ser Val Asp Glu
65 70 75 80

Ala Ile Ala Ala Cys Gly Asp Glu Pro Glu Ile Met Val Ile Gly Gly
85 90 95

Gly Arg Val Tyr Glu Gln Phe Leu Pro Lys Ala Gln Lys Leu Tyr Leu
100 105 110

Thr His Ile Asp Ala Glu Val Glu Gly Asp Thr His Phe Pro Asp Tyr
115 120 125

Glu Pro Asp Asp Trp Glu Ser Val Phe Ser Glu Phe His Asp Ala Asp
130 135 140

Ala Gln Asn Ser His Ser Tyr Cys Phe Glu Ile Leu Glu Arg Arg
145 150 155

<210> SEQ ID NO 8
<211> LENGTH: 160
<212> TYPE: PRT
<213> ORGANISM: Artificial Sequence
<220> FEATURE:
<223> OTHER INFORMATION: Primer that can hybridise to flanking regions of pig microsatellites sequences
<220> FEATURE:
<223> OTHER INFORMATION: Primer that can hybridise to flanking regions of pig microsatellites sequences
<220> FEATURE:
<223> OTHER INFORMATION: Primer that can hybridise to flanking regions of pig microsatellites sequences

<400> SEQUENCE: 8

Met Thr Phe Ser Leu Ile Val Ala Thr Thr Leu Asn Ser Val Ile Gly
1 5 10 15

Lys Asp Asn Gln Met Pro Trp His Leu Pro Ala Asp Leu Ala Trp Phe
20 25 30

Arg Gln Asn Thr Thr Gly Lys Pro Val Ile Met Gly Arg Lys Thr Phe
35 40 45

Glu Ser Ile Gly Arg Pro Leu Pro Lys Arg Thr Asn Ile Val Leu Ser
50 55 60

Arg Gln Pro Phe Lys His Glu Gly Val Val Trp Lys Asn Ser Leu Glu
65 70 75 80

Ser Ala Val Asn Phe Val Arg Asp Phe Asp Glu Ile Met Leu Ile Gly
85 90 95

Gly Gly Glu Leu Phe Lys Gln Tyr Leu Pro Lys Ala Asp Lys Leu Tyr
100 105 110

Leu Thr Gln Ile Gln Thr Glu Leu Asp Gly Asp Thr Phe Phe Pro Gln
115 120 125

Leu Asn Trp Glu Glu Trp Lys Ile Glu Phe Asp Glu Tyr His Lys Ala
130 135 140

Asp Glu Gln Asn Arg Tyr Asp Cys Arg Ser Leu Ile Leu Thr Arg Lys
145 150 155 160

-continued

```
<210> SEQ ID NO 9
<211> LENGTH: 168
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 9

Met Ile Ser Phe Ile Phe Ala Met Asp Ala Asn Arg Leu Ile Gly Lys
  1               5                  10                  15

Asp Asn Asp Leu Pro Trp His Leu Pro Asn Asp Leu Ala Tyr Phe Lys
             20                  25                  30

Lys Ile Thr Ser Gly His Ser Ile Ile Met Gly Arg Lys Thr Phe Glu
         35                  40                  45

Ser Ile Gly Arg Pro Leu Pro Asn Arg Lys Asn Ile Val Val Thr Ser
     50                  55                  60

Ala Pro Asp Ser Glu Phe Gln Gly Cys Thr Val Val Ser Ser Leu Lys
 65                  70                  75                  80

Asp Val Leu Asp Ile Cys Ser Gly Pro Glu Glu Cys Phe Val Ile Gly
                 85                  90                  95

Gly Ala Gln Leu Tyr Thr Asp Leu Phe Pro Tyr Ala Asp Arg Leu Tyr
            100                 105                 110

Met Thr Lys Ile His His Glu Phe Glu Gly Asp Arg His Phe Pro Glu
        115                 120                 125

Phe Asp Glu Ser Asn Trp Lys Leu Val Ser Ser Glu Gln Gly Thr Lys
    130                 135                 140

Asp Glu Lys Asn Pro Tyr Asp Tyr Glu Phe Leu Met Tyr Glu Lys Lys
145                 150                 155                 160

Asn Ser Ser Lys Val Gly Gly Phe
                165


<210> SEQ ID NO 10
<211> LENGTH: 168
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 10

Met Ile Ile Gly Ile Trp Ala Glu Asp Glu Gln Gly Leu Ile Gly Glu
  1               5                  10                  15

Ala Asp Lys Met Pro Trp Ser Leu Pro Ala Glu Gln Lys His Phe Lys
             20                  25                  30

Glu Thr Thr Met Asn Gln Val Ile Leu Met Gly Arg Lys Thr Phe Glu
         35                  40                  45

Gly Met Asn Lys Arg Val Leu Pro Gly Arg Ile Ser Ile Thr Leu Thr
     50                  55                  60
```

-continued

```
Arg Asp Glu Thr Tyr Gln Ser Glu Asn Glu Lys Val Leu Ile Met His
 65                  70                  75                  80

Ser Pro Lys Glu Val Leu Asp Trp Tyr Tyr Lys Gln Asp Lys Asp Leu
                 85                  90                  95

Phe Ile Thr Gly Gly Ala Glu Ile Leu Ala Leu Phe Glu Ser Glu Leu
            100                 105                 110

Glu Leu Leu Tyr Arg Thr Val Val His Glu Lys Phe Gln Gly Asp Thr
        115                 120                 125

Tyr Phe Pro Thr His Phe Asp Phe Gly Lys Phe Lys Val Val Ser Glu
    130                 135                 140

Ile Phe His Asp Lys Asp Glu Arg Asn Ala Tyr Thr Phe Thr Ile Lys
145                 150                 155                 160

Lys Tyr Glu Lys Val Lys Gln Pro
                165
```

<210> SEQ ID NO 11
<211> LENGTH: 163
<212> TYPE: PRT
<213> ORGANISM: Artificial Sequence
<220> FEATURE:
<223> OTHER INFORMATION: Primer that can hybridise to flanking regions of pig microsatellites sequences
<220> FEATURE:
<223> OTHER INFORMATION: Primer that can hybridise to flanking regions of pig microsatellites sequences
<220> FEATURE:
<223> OTHER INFORMATION: Primer that can hybridise to flanking regions of pig microsatellites sequences

<400> SEQUENCE: 11

```
Met Thr Ala Phe Leu Trp Ala Gln Asp Arg Asp Gly Leu Ile Gly Lys
  1               5                  10                  15

Asp Gly His Leu Pro Trp His Leu Pro Asp Asp Leu His Tyr Phe Arg
             20                  25                  30

Ala Gln Thr Val Gly Lys Ile Met Val Val Gly Arg Arg Thr Tyr Glu
         35                  40                  45

Ser Phe Pro Lys Arg Pro Leu Pro Glu Arg Thr Asn Val Val Leu Thr
     50                  55                  60

His Gln Glu Asp Tyr Gln Ala Gln Gly Ala Val Val Val His Asp Val
 65                  70                  75                  80

Ala Ala Val Phe Ala Tyr Ala Lys Gln His Pro Asp Gln Glu Leu Val
                 85                  90                  95

Ile Ala Gly Gly Ala Gln Ile Phe Thr Ala Phe Lys Asp Asp Val Asp
            100                 105                 110

Thr Leu Leu Val Thr Arg Leu Ala Gly Ser Phe Glu Gly Asp Thr Lys
        115                 120                 125

Met Ile Pro Leu Asn Trp Asp Asp Phe Thr Lys Val Ser Ser Arg Thr
    130                 135                 140

Val Glu Asp Thr Asn Pro Ala Leu Thr His Thr Tyr Glu Val Trp Gln
145                 150                 155                 160

Lys Lys Ala
```

<210> SEQ ID NO 12
<211> LENGTH: 181
<212> TYPE: PRT
<213> ORGANISM: Artificial Sequence
<220> FEATURE:
<223> OTHER INFORMATION: Escherichia coli DHFR deficient strain
<220> FEATURE:
<223> OTHER INFORMATION: Primer that can hybridise to flanking regions -continued

```
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 12

Met Thr Arg Ala Glu Val Gly Leu Val Trp Ala Gln Ser Thr Ser Gly
  1               5                  10                  15

Val Ile Gly Arg Gly Gly Asp Ile Pro Trp Ser Val Pro Glu Asp Leu
            20                  25                  30

Thr Arg Phe Lys Glu Val Thr Met Gly His Thr Val Ile Met Gly Arg
        35                  40                  45

Arg Thr Trp Glu Ser Leu Pro Ala Lys Val Arg Pro Leu Pro Gly Arg
     50                  55                  60

Arg Asn Val Val Val Ser Arg Arg Pro Asp Phe Val Ala Glu Gly Ala
 65                  70                  75                  80

Arg Val Ala Gly Ser Leu Glu Ala Ala Leu Ala Tyr Ala Gly Ser Asp
                 85                  90                  95

Pro Ala Pro Trp Val Ile Gly Gly Ala Gln Ile Tyr Leu Leu Ala Leu
            100                 105                 110

Pro His Ala Thr Arg Cys Glu Val Thr Glu Ile Glu Ile Asp Leu Arg
        115                 120                 125

Arg Asp Asp Asp Asp Ala Leu Ala Pro Ala Leu Asp Asp Ser Trp Val
    130                 135                 140

Gly Glu Thr Gly Glu Trp Leu Ala Ser Arg Ser Gly Leu Arg Tyr Arg
145                 150                 155                 160

Phe His Ser Tyr Arg Arg Asp Pro Arg Ser Ser Val Arg Gly Cys Ser
                165                 170                 175

Pro Ser Arg Pro Ser
            180


<210> SEQ ID NO 13
<211> LENGTH: 161
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 13

Met Thr Leu Ser Ile Ile Val Ala His Asp Lys Gln Arg Val Ile Gly
  1               5                  10                  15

Tyr Gln Asn Gln Leu Pro Trp His Leu Pro Asn Asp Leu Lys His Ile
            20                  25                  30

Lys Gln Leu Thr Thr Gly Asn Thr Leu Val Met Ala Arg Lys Thr Phe
        35                  40                  45

Asn Ser Ile Gly Lys Pro Leu Pro Asn Arg Arg Asn Val Val Leu Thr
     50                  55                  60

Asn Gln Ala Ser Phe His His Glu Gly Val Asp Val Ile Asn Ser Leu
 65                  70                  75                  80

Asp Glu Ile Lys Glu Leu Ser Gly His Val Phe Ile Phe Gly Gly Gln
```

-continued

```
                 85                  90                  95

Thr Leu Tyr Glu Ala Met Ile Asp Gln Val Asp Asp Met Tyr Ile Thr
            100                 105                 110

Val Ile Asp Gly Lys Phe Gln Gly Asp Thr Phe Phe Pro Pro Tyr Thr
        115                 120                 125

Phe Glu Asn Trp Glu Val Glu Ser Ser Val Glu Gly Gln Leu Asp Glu
    130                 135                 140

Lys Asn Thr Ile Pro His Thr Phe Leu His Leu Val Arg Arg Lys Gly
145                 150                 155                 160

Lys


<210> SEQ ID NO 14
<211> LENGTH: 15
<212> TYPE: PRT
<213> ORGANISM: Artificial Sequence
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences
<220> FEATURE:
<223> OTHER INFORMATION: Primer that can hybridise to flanking regions
      of pig microsatellites sequences

<400> SEQUENCE: 14

Ser Met Ser Leu Ile Xaa Ala Gln Xaa Thr Gly Gly Ile Ile Ser
  1               5                  10                  15
```